US010809260B2

(12) United States Patent
Baird et al.

(10) Patent No.: US 10,809,260 B2
(45) Date of Patent: Oct. 20, 2020

(54) METHOD AND KIT FOR DETECTION OF MYCOBACTERIA

(71) Applicant: Diagnostig LTD, Bangor Gwynedd (GB)

(72) Inventors: Mark Stephen Baird, Gwynedd (GB); Christopher David Gwenin, Gwynedd (GB); Vanessa Valerie Gwenin, Gwynedd (GB); Alison Jones, Gwynedd (GB)

(73) Assignee: DIAGNOSTIG LTD, Gwynedd (GB)

( * ) Notice: Subject to any disclaimer, the term of this patent is extended or adjusted under 35 U.S.C. 154(b) by 51 days.

(21) Appl. No.: 15/503,647

(22) PCT Filed: Aug. 13, 2015

(86) PCT No.: PCT/GB2015/052340
§ 371 (c)(1),
(2) Date: Feb. 13, 2017

(87) PCT Pub. No.: WO2016/024118
PCT Pub. Date: Feb. 18, 2016

(65) Prior Publication Data
US 2017/0242005 A1      Aug. 24, 2017

(30) Foreign Application Priority Data

Aug. 13, 2014  (GB) .................................. 1414369.7

(51) Int. Cl.
| A61K 39/00 | (2006.01) |
| A61K 39/02 | (2006.01) |
| A61K 39/04 | (2006.01) |
| G01N 33/569 | (2006.01) |
| G01N 33/543 | (2006.01) |
| G01N 33/558 | (2006.01) |
| G01N 33/553 | (2006.01) |
| G01N 33/92 | (2006.01) |

(52) U.S. Cl.
CPC ....... *G01N 33/5695* (2013.01); *G01N 33/543* (2013.01); *G01N 33/54366* (2013.01); *G01N 33/553* (2013.01); *G01N 33/558* (2013.01); *G01N 33/92* (2013.01); *G01N 2333/35* (2013.01); *G01N 2405/00* (2013.01); *G01N 2800/50* (2013.01)

(58) Field of Classification Search
CPC ..................................................... A61K 39/04
USPC ........... 424/184.1, 234.1, 248.1; 435/7.1, 7.2
See application file for complete search history.

(56) References Cited

U.S. PATENT DOCUMENTS

| 5,721,109 A | 2/1998 | Yana et al. |
| 7,122,577 B1 | 10/2006 | Verschoor et al. |
| 9,506,921 B2 * | 11/2016 | Gwenin ............. G01N 33/5695 |
| 2007/0054335 A1 | 3/2007 | Esfandiari et al. |

FOREIGN PATENT DOCUMENTS

| EP | 0921397 A1 | 8/1997 |
| JP | H07248329 A | 9/1995 |
| WO | 9839025 A2 | 9/1998 |
| WO | 2005116654 A1 | 12/2005 |
| WO | 2010086667 A2 | 8/2010 |
| WO | 2012007903 A2 | 1/2012 |
| WO | 2012131394 A1 | 10/2012 |
| WO | WO2012/131394 A1 * | 10/2012 |
| WO | 2013186679 A1 | 12/2013 |
| WO | 2014210327 A1 | 12/2014 |

OTHER PUBLICATIONS

GB Search Report for GB Application No. GB1514411.6 dated May 26, 2016, 4 pages.
International Preliminary Report on Patentability for corresponding PCT Application No. PCT/GB2015/052340, dated Feb. 23, 2017, 6 pages.
International Search Report and Written Opinion for corresponding PCT Application No. PCT/GB2015/052340 dated Oct. 29, 2015, 9 pages.
GB Search Report and Written Opinion for corresponding GB Application No. GB1414369.7 dated Oct. 23, 2015, 5 pages.

* cited by examiner

*Primary Examiner* — Rodney P Swartz
(74) *Attorney, Agent, or Firm* — Hoffman Warnick LLC

(57) ABSTRACT

A method of determining whether an individual is infected with mycobacteria. The method comprising the steps of (a) providing a system which comprises at least two different mycolic-acid derived antigens; (b) introducing a sample obtained from the individual into the system and into contact with each of the at least two different mycolic-acid derived antigens; and (c) detecting the presence or absence of the binding of a biomarker in the sample with each antigen in the system. The method may be particularly suitable for determining the presence or absence of a disease antibody indicative of infection with any disease caused by infection with mycobacteria, for example *tuberculosis*, leprosy, pulmonary disease, burili ulcer, Johne's disease and bovine *tuberculosis*. A kit and device are also described. The present invention may provide an over the counter device to allow individuals to check on a routine basis that they have normal immune responses.

11 Claims, 4 Drawing Sheets

METHOD AND KIT FOR DETECTION OF MYCOBACTERIA

The present invention relates to a kit and method for determining whether or not an individual is infected with a mycobacterial disease.

Pathogenic and non-pathogenic mycobacteria are very widespread in the environment and their rapid detection and distinction represents an important public health target.

For example, *tuberculosis* is a serious and often fatal disease which affects humans and other animals and is caused by infection with mycobacteria. Infection with *Mycobacterium tuberculosis* is very common and it is estimated that up to a third of the world's population is infected with the bacterium. Most of those infected will never develop the active disease but because it is often fatal if left untreated, early diagnosis of the disease is essential. Methods of detecting *M. tuberculosis* are known but these existing methods have a number of disadvantages. It can often take a long time for the results of a test to be known, the equipment needed is expensive or difficult to use and the results are not always reliable. A number of serodiagnostic assays have been developed for the diagnosis of *tuberculosis* but none of these have been assessed as reaching the standards required by the World Health Organisation.

Infection with *tuberculosis* is also common in cattle and bovine *tuberculosis* is recognised as a serious problem. Another disease common in cattle is Johne's disease which is caused by infection with another mycobacteria, *Mycobacterium avium paratuberculosis*. There have been some studies suggesting that Crohn's disease in humans may be linked to ingestion of food infected with *M. avium*.

Infectious diseases, for example *tuberculosis*, can cause a person or animal infected with the disease to produce antibodies. Identification of these antibodies in a sample taken from an infected individual can lead to a diagnosis of the disease.

However, the diagnosis of infection with *Mycobacterium tuberculosis* is not straightforward due to the complexity of the disease. Patients often present with co-infection with HIV and this can significantly change their blood biochemistry and the availability of sputum samples. People living in areas of the world where infection with mycobacteria is common have different background levels of antibodies in their blood and many will be infected with latent *tuberculosis*.

One problem with many diagnostic methods of the prior art is that they fail to distinguish between latent *tuberculosis* and active disease. It can also be very difficult to diagnose *tuberculosis* in children.

In addition, infection with *Mycobacterium tuberculosis* can sometimes be difficult to rapidly differentiate from infection with other mycobacteria, for example *Mycobacterium avium*.

Due to these complexities it has been difficult to find a satisfactory method of accurately diagnosing infection with *Mycobacterium tuberculosis*. The current "gold standard" method of confirming infection with *tuberculosis* is by growing a culture from a sample. However this is a complex and expensive method and it can take a number of weeks to confirm a diagnosis. Thus culture methods are unsuitable for use in environments with limited access to laboratory facilities and in many cases a quick diagnosis is essential.

It is an aim of the present invention to provide a kit, method and device for detecting infection with mycobacteria which is less expensive and has improved reliability compared with methods of the prior art. It is also desirable to find a method. kit or device which can reliably distinguish between infection with different types of mycobacteria.

According to a first aspect of the present invention, there is provided a method of determining whether an individual is infected with mycobacteria, the method comprising:
 (a) providing a system which comprises at least two different mycolic-acid derived antigens;
 (b) introducing a sample obtained from the individual into the system and into contact with each of the at least two different mycolic-acid derived antigens; and
 (c) detecting the presence or absence of the binding of a biomarker in the sample with each antigen in the system.

Suitably steps (a), (b) and (c) are carried out in the order (a) followed by (b) followed by (c).

The method may additionally or alternatively provide a method of determining whether an individual is infected with organisms, other than mycobacteria, which produce mycolic acid related molecules.

The at least two different mycolic-acid derived antigens may be present on one or more substrates in the system and/or in one or more solutions in the system. The at least two different mycolic-acid derived antigens may be encapsulated in the system, for example in liposomes.

Suitably the at least two different mycolic-acid derived antigens are separated within the system, for example by being located at different positions on a substrate within the system, by being carried on different substrates within the system or by being present in different solutions held separately within the system. Therefore the sample may be brought into contact with each of the at least two different mycolic-acid derived antigens individually in order to allow the detection of the presence or absence of the binding of a biomarker in the sample with each antigen separately.

In some embodiments, the at least two different mycolic-acid derived antigens are bound to a substrate in the system. Suitably the system comprises at least one substrate. Suitably the at least two different mycolic-acid derived antigens are each bound to the same substrate.

The system may comprise more than one substrate. Suitably each of the at least two different mycolic-acid derived antigens are each bound to different substrates.

In alternative embodiments, the at least two different mycolic-acid derived antigens are present in different solutions in the system.

Suitably the system comprises a substrate which carries the at least two different mycolic-acid derived antigens at different positions on the substrate.

Suitably the method comprises the steps of:
 (a) providing a substrate which carries at least two different mycolic-acid derived antigens at different positions;
 (b) contacting the substrate with a sample obtained from the individual; and
 (c) detecting the presence or absence of the binding of a biomarker in the sample with each antigen at each position on the substrate.

Suitably steps (a), (b) and (c) are carried out in the order (a) followed by (b) followed by (c).

Suitably, according to this first aspect of the present invention there is provided a method of determining whether an individual is infected with mycobacteria, the method comprising:
 (a) providing a substrate which carries at least two different mycolic-acid derived antigens at different positions;

(b) contacting the substrate with a sample obtained from the individual; and (c) detecting the presence or absence of the binding of a biomarker in the sample with each antigen at each position on the substrate.

Suitably steps (a), (b) and (c) are carried out in the order (a) followed by (b) followed by (c).

Preferably the present invention provides a method of determining whether an individual is infected with a mycobacterial disease. The method may involve detection of a biomarker in the sample that is indicative of infection with a mycobacterial disease. In some embodiments the method may involve detecting a biomarker which is indicative of infection with mycobacteria but which does not necessarily mean the individual has an active disease. For example the present invention may provide a method of detecting an unusual immune response in an individual.

The biomarker is suitably an antibody.

The present invention preferably relates to a method of determining the presence or absence in a sample of an antibody indicative of infection with or exposure to mycobacteria. The sample may be taken form any individual suspected of infection with a mycobacterial disease. In preferred embodiments the individual is a mammal. It may be a ruminant, for example a cow. In some preferred embodiments the individual is a human.

Suitably the invention involves determining the presence or absence of a disease antibody indicative of infection with any disease caused by infection with mycobacteria. Examples of such diseases include *tuberculosis*, leprosy, pulmonary disease, burili ulcer, Johne's disease and bovine *tuberculosis*.

In preferred embodiments the method of the present invention is used to determine the presence or absence of an antibody indicative of infection with *Mycobacterium tuberculosis* and/or *Mycobacterium avium paratuberculosis*.

The invention finds particular utility in determining the presence or absence in a sample of disease antibodies indicative of the presence of *tuberculosis*.

Step (a) of the method of the first aspect of the present invention may involve providing a substrate which carries at least two different mycolic-acid derived antigens at different positions.

The nature of the substrate will depend on the exact structure of the system. Suitable substrates are further described herein. For the avoidance of doubt the term substrate as used in relation to step (a) of the method of the first aspect refers to a carrier for the antigens, for example a solid carrier. It is typically a plate or sheet-like material. In some embodiments the substrate is a gel.

The antigen is suitably immobilised on the surface of the substrate, for example as is further described herein.

The antigen may be encapsulated, for example in a liposome.

The substrate may carry two or more different mycolic acid-derived antigens at different locations. By this we mean that a first mycolic acid derived antigen is located at a first position on the substrate and a second mycolic acid derived antigen is located at a second position on the substrate. There may be a mixture of mycolic acids at each position. The first and second mycolic acid-derived antigens are different to each other.

In some preferred embodiments the substrate is a porous substrate.

Preferably each antigen is selected from mycolic acids, derivatives and salts of mycolic acids and wax esters analogous to mycolic acids and derivatives and salts thereof.

Mycolic acids are long chain fatty acid compounds typically having 60 to 90 carbon atoms and are found as components of the cells of mycobacteria.

Two moieties can be distinguished in each mycolic acid: the main branch, or meromycolate moiety, and the mycolic motif, an α-alkyl β-hydroxy acid. The structure of the mycolic motif is common to each naturally occurring mycolic acid, except for minor variations in the length of the chain in the α-position. The two stereocentres in the α and β positions relative to the carboxylic group present in all natural mycolic acids have, when examined, always been found to both be in the (R)-configuration in these natural products. On the other hand, the meromycolate section, which generally contains two functionalities and three long chains (a, b, c in formula I), can be differently substituted in both the proximal (the one nearer the hydroxy-acid) and the distal position (further from the carboxylic acid).

Formula I

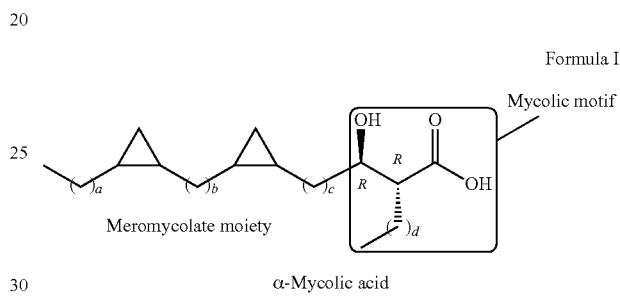

α-Mycolic acid

The mycolic acids are broadly separated into classes, according to the groups present in the meromycolate moiety. The proximal or distal functional groups can include cyclopropanes, double bonds, an epoxy group, a methoxy group, carbonyl group, carboxyl group or methyl group.

Examples of classes of mycolic acids (which in this specification may be referred to as MA) are shown in formula II and include α-MA (1), methoxy-MA (2), and keto-MA (3) all containing a cis-cyclopropane proximal to the hydroxy-acid; and corresponding structures (4) containing a proximal α-methyl-trans-cyclopropane.

Formula II

Me(CH$_2$)$_a$ (CH$_2$)$_b$ (CH$_2$)$_c$CHOHCHCOOH
Me(CH$_2$)$_d$ (1)

Me  OMe
Me(CH$_2$)$_a$  (CH$_2$)$_b$  (CH$_2$)$_c$CHOHCHCOOH
Me(CH$_2$)$_d$ (2)

Me  O
Me(CH$_2$)$_a$  (CH$_2$)$_b$  (CH$_2$)$_c$CHOHCHCOOH
Me(CH$_2$)$_d$ (3)

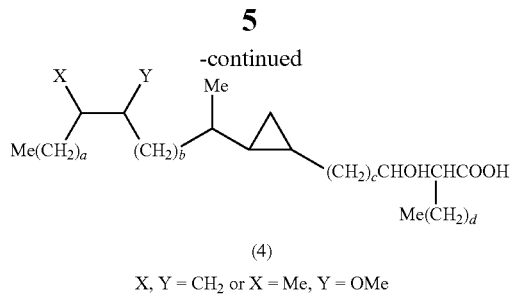

(4)

X, Y = CH₂ or X = Me, Y = OMe a = 15, 17, 18, 19
b = 10, 14, 16
c = 11, 15, 17, 19, 21
d = 21, 23

Such compounds are antigens for lipid antibodies generated by infection with mycobacteria.

Each of the two or more antigens is suitably selected from one or more of the following classes of compounds:
(i) mycolic acids obtained from natural sources;
(ii) synthetically prepared mycolic acids;
(iii) salts of mycolic acids;
(iv) esters of mycolic acids (i) and/or (ii);
(v) sulfur-containing mycolic acid compounds and/or salts or esters thereof; and
(vi) simple structural analogues of mycolic acids and/or salts or esters thereof; and
(vii) mycolic acid wax esters and/or salts or esters thereof.

Mycolic acids obtained from natural sources (i) are typically available as mixtures. These typically contain different classes of mycolic acids and each class will usually contain a complex mixture of different homologues.

It is highly advantageous to use synthetically prepared mycolic acids (ii) since these are available as single compounds in high purity (for example greater than 95% or greater than 99%). The use of single compounds allows greater selectivity to be achieved.

Salts of natural mycolic acids and/or synthetic mycolic acids (iii) may be useful. Suitable salts include ammonium, alkali metal and alkaline earth metal salts, for example salts of lithium, potassium, sodium, calcium or barium.

Suitable esters (iv) for use as antigens include esters of simple monohydric and polyhydric alcohols and sugar esters. Suitable esters include glycerol esters of mycolic acids. Some particularly preferred antigens are sugar esters of mycolic acids. Some naturally occurring sugar esters of mycolic acids are trehalose monomycolates or trehalose dimycolates (also known as cord factors). Cord factors can be isolated as complex mixtures from natural sources. Esters of mycolic acids for use herein as antigens may be synthetically prepared. They may be prepared by esterification of synthetically prepared mycolic acids or by esterification of mycolic acids isolated from natural sources.

By sulfur-containing mycolic acid compounds and/or esters or salts thereof (v) we mean to refer to synthetic compounds which are analogues of natural mycolic acid compounds rather than naturally occurring compounds that contain sulfur. Wax esters containing a sulfur atom may also be used. Suitable sulfur-containing mycolic acid derivatives may include any compound in which one or more carbon atoms and/or one or more oxygen atoms of a mycolic acid derived compound have been replaced by a sulfur atom. Sulfur-containing mycolic acid derivatives also include compounds in which a hydrogen substituent has been replaced with a moiety "SX" wherein X is hydrogen, $SR^1$ or $COR^2$ in which $R^1$ is an optionally substituted alkyl, alkenyl, acyl, aryl group, mycolic acid or sugar ester and $R^2$ is an optionally substituted alkyl, alkenyl or aryl group.

In some embodiments the sulfur-containing ester of a mycolic acid may be an ester of a disaccharide in which one saccharide unit is bonded to mycolic acid and the other is bonded to a sulfur-containing fatty acid.

Simple structural analogues of mycolic acids and/or esters or salts thereof (vi) which may be used herein as antigens include compounds which include fewer functional groups and/or stereocentres than are found in natural mycolic acid compounds but have many structural features in common, for example they include a similar number of carbon atoms and have a simpler substitution pattern.

Mycolic acid wax esters (vii) include a cyclopropyl or an alkene group and an internal ester group. These can be isolated from natural sources (typically as mixtures of homologues) or they can be prepared synthetically. Salts and esters of these wax esters thereof can also be used.

Preferably each antigen is selected from mycolic acids, wax esters and salts and esters thereof. Preferably the antigen is a synthetically prepared antigen.

Suitably each antigen is selected from mycolic acids, wax esters and esters thereof. Preferably each antigen is a synthetically prepared antigen.

When the antigen is an ester preferably the mycolic acid or wax ester residue or residues present in the ester are derived from synthetically prepared mycolic acids/wax esters.

Synthetically prepared antigens are preferred as they can be prepared in high purity.

Suitable mycolic acid classes for use herein as antigens include keto mycolic acids having the structure shown in formula IIa; hydroxy mycolic acids having the structure shown in formula IIb; alpha mycolic acids having the structure shown in formula IIc; and methoxy mycolic acids having the structure shown in formula IId. Such mycolic acids may be included directly as the free acid or as an ester or salt thereof. In preferred embodiments the mycolic acid antigens are esters.

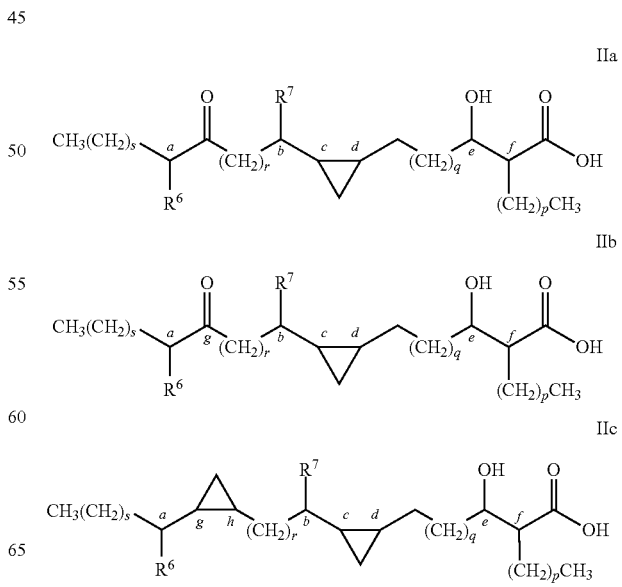

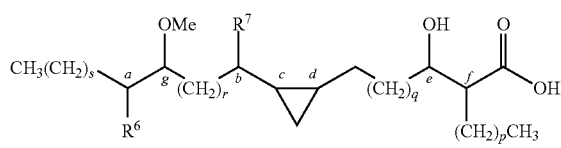

IId

In each of the structures IIa, IIb, IIc and IId $R^6$ may be hydrogen or $C_1$ to $C_4$ alkyl. Preferably $R^6$ is hydrogen or methyl.

In each of the structures IIa, IIb, IIc and IId $R^7$ may be hydrogen or $C_1$ to $C_4$ alkyl. Preferably $R^7$ is hydrogen or methyl.

In each of the structures IIa, IIb, IIc and IId p is preferably from 4 to 40, preferably from 8 to 36, more preferably from 12 to 32, for example from 16 to 30, more preferably from 20 to 28, for example from 22 to 26.

In the structures IIa, IIb, IIc and IId q is preferably from 2 to 40, more preferably from 4 to 36, for example from 6 to 30, preferably from 8 to 24, for example from 10 to 20 and preferably from 12 to 18.

In the structures IIa, IIb, IIc and IId, r is preferably from 2 to 40, for example from 6 to 36, preferably from 10 to 32, for example from 12 to 28, and preferably from 14 to 24.

In the structures IIa, IIb, IIc and IId, s is preferably from 2 to 40, for example from 6 to 36, preferably from 10 to 32, for example from 12 to 28, and preferably from 14 to 24.

In the structures IIa, IIb, IIc and IId, each of the chiral centres indicated at a, b, c, d, e, f, g and h may independently have either an (R) or an (S) configuration. Each cyclopropyl group may have either absolute stereochemistry and may have a trans or a cis configuration.

Any of the stereocentres indicated by a, b, c, d, e, f, g or h may be racemic. In the case of structure IIa it is possible that the stereocentre designated a will be racemic as this is a readily epimerisable position.

In addition to the compounds illustrated by the structures IIa, IIb, IIc and IId, other classes of mycolic acids may be useful as antigens in the present invention. Suitable mycolic acid compounds may include an alkene functional group instead of the proximal cyclopropyl group shown in formulas IIa, IIb, IIc and IId. Further suitable classes of mycolic acid include those substituted with epoxy and alkene groups in the meromycolate moiety in place of the distal cyclopropyl, methoxy, hydroxyl or keto functional group. The proximal group in such compounds may be cyclopropyl or alkene. The structure of such further suitable mycolic acid compounds will be known to the person skilled in the art.

Each antigen used in the method of the present invention is preferably a mycolic acid-derived antigen selected from keto mycolic acids, hydroxy mycolic acids, alpha mycolic acids, methoxy mycolic acids, epoxy mycolic acids and alkene mycolic acids.

Each of the above-described mycolic acid compounds may be used as single compounds prepared synthetically and/or may be included in mixtures of synthetic compounds and/or may be included in mixtures isolated from natural sources. Any of these compounds could be used in the preparation of synthetic esters or be present in naturally occurring esters such as cord factors.

In some embodiments the system comprises an antigen which is an ester of a mycolic acid. Suitably the mycolic acid is not a mycolic acid found in or isolated from *Mycobacterium tuberculosis*.

Suitable esters include esters of monohydric alcohols, polyhydric alcohols and sugars.

Ester antigens for use herein may be monoesters, diesters or polyesters. Each ester may include one or more mycolic acid groups and one or more alcohol or sugar moieties. Antigens which are mixed esters including alcohols and sugars may also be used, for example compounds including an alcohol ester moiety and a sugar ester moiety.

Some preferred antigens for use in the present invention are sugar esters of a mycolic acid.

When a sugar ester is present this may be a monosaccharide, disaccharide or an oligosaccharide.

Suitable sugar units which may be included are those based on hexoses and those based on pentoses.

Suitable sugar esters for use herein are compounds of formula (III):

$$(M)_x-(S)_y-(M')_z \qquad (III)$$

wherein x is from 1 to 6, y is from 1 to 12, z is from 0 to 10, each M and each M' is independently a mycolic acid residue including a δ-hydroxy acid moiety and each S is a monosaccharide unit.

In some embodiments x is from 1 to 4, preferably from 1 to 3, more preferably x is 1 or 2 and most preferably x is 1.

When x is greater than 1 and y is greater than 1, each M may be bonded to the same or different monosaccharide unit.

In some embodiments z is 0 to 6, preferably 0 to 4, more preferably 0 to 2, for example 0 or 1. In some embodiments preferably z is 1.

When z is greater than 1 and y is greater than 1, each M' may be bonded to the same or different monosaccharide unit.

Each M or M' is a mycolic acid residue. By this we mean to refer to the portion of the acid molecule other than the acidic proton.

Each M and M' may be the same or different. When x is greater than 1, each M may be the same or different. When z is greater than 1, each M' may be the same or different.

The compounds of formula (III) are sugar esters of mycolic acid. Thus each acidic unit of the mycolic acid residues M and/or M' is bonded to an alcoholic group of a monosaccharide unit to form an ester linkage. Preferably each M and/or M' is bonded to a primary alcoholic group of a monosaccharide unit.

Suitable sugar ester compounds include monomycolates, dimycolates, trimycolates and tetramycolates; and mixed esters of sugar and alcohols.

In some embodiments y is between 1 and 6, preferably between 1 and 4, more preferably between 1 and 3. In some embodiments most preferably y is 1 or 2, especially 2.

In some embodiments the compound of formula (III) is an ester formed from one mycolic acid unit and one monosaccharide unit.

In some embodiments, the compound of formula (III) is an ester formed from one mycolic acid unit and two monosaccharide units wherein the two monosaccharide units are joined to form a disaccharide. Thus in such embodiments the compound of formula (III) is an ester formed from one mycolic acid unit and a disaccharide.

In some preferred embodiments, the compound of formula (III) is an ester formed from two mycolic acid units and two monosaccharides, that is two mycolic acid units and a disaccharide. In such cases, the compound has the formula M-S-S-M' in which each monosaccharide unit S may be the same or different.

In some preferred embodiments the ratio of mycolic acid units (M and M' combined total) to monosaccharide units(s) is approximately 1:1.

In some embodiments x+z=y.

Each S is monosaccharide unit. By monosaccharide unit we mean to include monosaccharides in which all of the non-binding hydroxyl groups are free and also monosaccharide moieties in which one or more of the hydroxyl groups are protected. Suitable protecting groups are known to the person skilled in the art and including, for example, methyl ethers.

Preferably the or each monosaccharide unit S has from 3 to 8 carbon atoms, preferably 5 or 6. In some embodiments the or each monosaccharide unit has 6 carbon atoms. In preferred embodiments the or each monosaccharide unit S is an aldose.

Suitably each S is independently selected from allose, altrose, galactose, glucose, gulose, idose, mannose, talose, fructose, psicose, sorbose, and tagatose. Each S may be independently selected from allose, altrose, galactose, glucose, gulose, idose, mannose and talose. In some embodiments each S is independently selected from glucose and mannose. In some preferred embodiments each S is glucose.

Each monosaccharide unit may be present as the D or L isomer. Preferably each is present as the natural D isomer. Each monosaccharide unit may be present as the α form or the β form.

In some embodiments, y is 2 and the compound of formula (III) includes a disaccharide unit. In such a disaccharide unit, the monosaccharides may be connected in any suitable way. As the skilled person will appreciate, the nature of the bonding between the two monosaccharide units will determine the nature of the disaccharide.

Suitably the disaccharide is selected from sucrose, lactose, maltose, trehalose, cellobiose, kojibiose, nigerose, isomaltose, sophorose, laminaribiose, gentiobiose, turanose, maltulose, palatinose, gentiobiulose, mannobiose, melibiose, melibiulose, rutinose, rutinulose and xylobiose.

In some preferred embodiments the disaccharide unit is selected from sucrose, lactose, maltose, trehalose, and cellobiose. One especially preferred disaccharide unit is trehalose.

Some especially preferred sugar esters for use herein are glucose esters.

Other especially preferred sugar esters are trehalose esters. Suitable trehalose esters include trehalose monomycolates and trehalose dimycolates. Trehalose dimycolates (or cord factors) have the structure shown in formula IV wherein MA represents the residue of a mycolic acid:

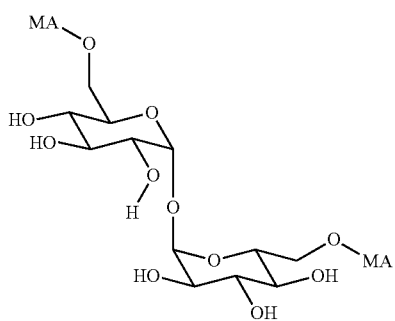

Formula IV

In formula IV each MA residue may be the same or a different mycolic acid.

In some embodiments the or each monosaccharide unit S is a pentose.

In some embodiments each S is an aldopentose. Suitably each S is independently selected from arabinose, lyxose, ribose and xylose. In some preferred embodiments each S is arabinose.

In some embodiments the antigen may be a compound of formula (III) in which eash S is an aldopentose, preferably arabinose, y is from 1 to 5 and x+z is from 1 to 4.

Some preferred arabinose esters compounds of formula (III) for use as antigens in the present invention include arabinose monomycolates, arabinose dimycolates, triarabinose dimycolate and pentarabinose tetramycolate. Arabinose monocycolates are especially preferred.

Some further preferred compounds for use as antigens in the present invention are mixed mycolic acid esters of sugars and monohydric or polyhydric alcohols, especially sugars and glycerol.

In some embodiments the system comprises one or more antigens which are keto mycolic acids or derivatives thereof.

In some embodiments the system comprises one or more antigens which are hydroxy mycolic acids or derivatives thereof.

In some embodiments the system comprises one or more antigens which are methoxy mycolic acids or derivatives thereof.

In some embodiments the system comprises one or more antigens which are alpha mycolic acids or derivatives thereof.

In some embodiments the system comprises one or more antigens which are epoxy mycolic acids or derivatives thereof.

In some embodiments the system comprises one or more antigens which are alkene mycolic acids or derivatives thereof.

Simple structural analogues of mycolic acids and wax esters which can be used herein as antigens include compounds having the structures indicated in formula IIa, IIb, IIc or IId in which some or all of the stereocentres a, b, c, d, e, f, g and h are racemic and in which $R^6$ and $R^7$ may each be hydrogen.

In some embodiments the antigen may be a mycolic acid wax ester. These compounds suitably have the formula (V):

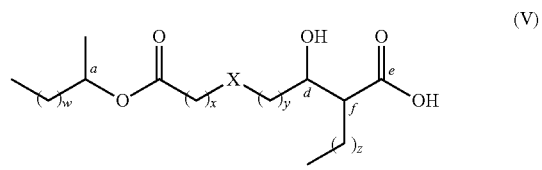

(V)

wherein w is from 2 to 40, x is from 2 to 40, y is from 2 to 40, z is from 4 to 40 and X is a three carbon fragment including an alkane, alkene or cyclopropyl moiety.

Suitably X is a group of formula (VIa), (VIb), (VIc) or (VId):

(VIa)

(VIb)

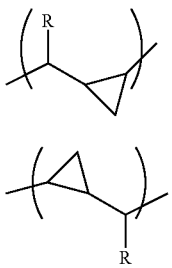

(VIc)

(VId)

wherein R is methyl or hydrogen.

The double bond in formula (VIa) and (VIb) may be cis or trans.

In embodiments in which X is (VIa) or (VIb), when the double bond is trans R is preferably methyl.

In embodiments in which the double bond is cis, R is preferably H.

The cyclopropyl group of fragment (VIc) or (VId) may be cis or trans.

In preferred embodiments in which X is (VIc) or (VId), R is preferably methyl.

In some especially preferred embodiments X is a fragment of formula (VIc) and the wax ester has the formula (VII):

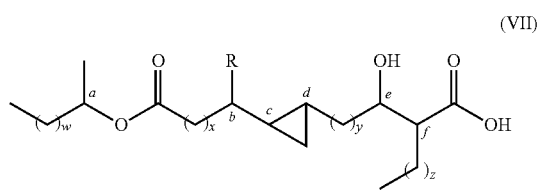

(VII)

Preferably w is from 10 to 32, preferably from 4 to 24; x is from 8 to 24, preferably from 12 to 18; y is from 10 to 32, preferably from 14 to 24; z is from 16 to 30; preferably from 22 to 26; and R is $C_1$ to $C_4$ alkyl, preferably methyl.

Esters of wax esters, for example sugar esters may also be used as antigens. The structures of the sugar esters are analogous to the sugar esters of the mycolic acids described above.

In some embodiments the antigen may be a mixed sugar ester including a sugar moiety, the residue of a mycolic acid and the residue of a wax ester.

In preferred embodiments each antigen is a synthetic antigen.

Suitably each antigen is at least 90% pure, for example at least 95% pure or at least 99% pure.

Preferably each antigen is a synthetic antigen which is at least 90%, preferably at least 95% or at least 99% pure.

By at least 90% pure we mean that at least 90% of the molecules of the antigen compound are identical i.e. the same homologue, the same stereoisomer and the same regioisomer.

In some embodiments a mixture of two or more antigens may be provided at one or more positions on the substrate. In preferred embodiments in which mixtures are present the structure of all compounds and preferably the relative amounts of each compound are known.

Preferred mixtures are mixtures of synthetically prepared antigens.

An advantage of using synthetically prepared antigens is that the compounds may be provided in high purity. Natural mycolic acids contain complex mixtures of different classes of mycolic acids and different homologues which are very difficult to separate. The use of synthetic compounds allows single compounds or known mixtures to be used. This enables antigens having a high degree of specificity and/or sensitivity for a particular antibody or antibodies to be used.

The system of the present invention comprises at least two different antigens.

In some preferred embodiments at least one of the antigens is an arabinose ester of a mycolic acid.

In some preferred embodiments at least one of the antigens is a trehalose ester of a mycolic acid.

In some embodiments at least one of the antigens is a glycerol ester of a mycolic acid.

In some embodiments at least one of the antigens is a glucose ester of a mycolic acid.

In some embodiments the at least two different mycolic-acid derived antigens comprise a trehalose monomycolate antigen and/or a trehalose dimycolate antigen.

In some embodiments the at least two different mycolic-acid derived antigens comprise an arabinose ester of a mycolic acid and a trehalose ester of a mycolic acid.

In some embodiments the at least two different mycolic-acid derived antigens comprise an arabinose ester of a mycolic acid, a trehalose monomycolate and a trehalose dimycolate.

In some embodiments the system comprises more than two mycolic-acid derived antigens at different positions. It may suitably comprise at least 3 different mycolic acid derived antigens at different positions, for example at least 4.

In some especially preferred embodiments the system comprises from 5 to 8 different antigens at different positions. Preferably each of these antigens is synthetically prepared. Preferably each is at least 90% pure, preferably at least 95% pure, for example at least 99% pure. The use of a combination of a number of different antigens allows a higher degree of sensitivity and specificity to be achieved and enables distinction between different mycobacterial diseases.

The present invention can be advantageously used not only to determine whether an individual is infected with a mycobacterial disease but also to distinguish between infection with different mycobacterial diseases. This is possible in both humans and animals, especially cows.

The combination of a number of antigens allows the discrimination between diseases and enables a greater degree of sensitivity and specificity to be achieved. In some embodiments data from large numbers of individuals can be collated to provide a reference library. Comparison of an individual sample with the known data can give a probability that the individual is infected with a particular disease.

Different antigens interact with different antibodies indicative of infection with different diseases. Thus the antigens are suitably selected to provide the best discrimination depending on the target disease or diseases.

The invention may also be used to detect abnormal immune responses. These may be the first indication that an individual is infected with mycobacteria and could be used to help prevent the onset of active disease. This could be particularly useful for screening populations at high risk of developing mycobacterial disease.

In some preferred embodiments the present invention provides a method of determining the likelihood that an individual is infected with one or more species of mycobacteria, the method comprising:
(a) providing a system which comprises at least two different mycolic-acid derived antigens;
(b) contacting the substrate with a sample obtained from the individual; and
(c) detecting the presence or absence of the binding of a biomarker in the sample with each antigen in the system.

Suitably the method of determining the likelihood that an individual is infected with one or more species of mycobacteria comprises the steps of:
(a) providing a substrate which carries at least two different mycolic-acid derived antigens at different positions;
(b) contacting the substrate with a sample obtained from the individual; and
(c) detecting the presence or absence of the binding of a biomarker in the sample with each antigen at each position on the substrate.

In such preferred embodiments the system comprises from 4 to 16, preferably from 6 to 12 different antigens.

Suitably the system comprises at least one trehalose monomycolate antigen.

Suitably the system comprises at least one trehalose dimycolate antigen.

Suitably the system comprises at least one glucose monomycolate antigen.

Suitably the system comprises at least one wax ester antigen.

Preferably the system comprises:
(a) a trehalose monomycolate antigen; and/or
(b) a trehalose dimycolate antigen.

The system may comprise more than one different (a) trehalose monomycolate antigen and/or more than one different (b) trehalose dimycolate antigen, for example comprising different mycolic acid residues or different chain lengths. Suitably the different (a) trehalose monomycolate antigens comprise different mycolic acid residues and/or the different (b) trehalose dimycolate antigens comprise different mycolic acid residues, for example selected from keto mycolic acids, alpha mycolic acids and methoxy mycolic acids.

Suitably the system comprises at least two different (a) trehalose monomycolate antigens and at least two different (b) trehalose dimycolate antigens.

In one embodiment the system comprises three different (a) trehalose monomycolate antigens and four different (b) trehalose dimycolate antigens. Suitably the system comprises:
(a1) a trehalose monomycolate antigen comprising an alpha mycolic acid residue;
(a2) a trehalose monomycolate antigen comprising a methoxy mycolic acid residue;
(a3) a trehalose monomycolate antigen comprising a methoxy mycolic acid residue which is different to the methoxy mycolic acid residue of (a2), for example a methoxy mycolic acid residue having the opposite stereochemistry in the meromycolate region to the methoxy mycolic acid residue of (a2);
(b1) a trehalose dimycolate antigen comprising two alpha mycolic acid residues, suitably identical alpha mycolic acid residues;
(b2) a trehalose dimycolate antigen comprising two keto mycolic acid residues, suitably identical keto mycolic acid residues;
(b3) a trehalose dimycolate antigen comprising two methoxy mycolic acid residues, suitably identical methoxy mycolic acid residues; and
(b4) a trehalose dimycolate antigen comprising two methoxy mycolic acid residues, suitably identical methoxy mycolic acid residues; which are different to the methoxy mycolic acid residues of (b3), for example methoxy mycolic acid residues having the opposite stereochemistry in the meromycolate region to the methoxy mycolic acid residues of (b3).

The system may comprise:
(a) a trehalose monomycolate antigen; and/or
(b) a trehalose dimycolate antigen; and
(c) a mycolic acid wax ester antigen.

The system may comprise more than one different (c) mycolic acid wax ester antigen, for example comprising different mycolic acid residues or different chain lengths. Suitably the more than one different (c) mycolic acid wax ester antigens comprise different mycolic acid residues, for example selected from keto mycolic acids, alpha mycolic acids and methoxy mycolic acids.

In one embodiment the system comprises at least two different (a) trehalose monomycolate antigens, for example comprising different mycolic acid residues or different chain lengths, and at least two different (c) mycolic acid wax ester antigens, for example comprising different mycolic acid residues or different chain lengths.

Suitably the system comprises at least two different (a) trehalose monomycolate antigens comprising different mycolic acid residues and at least two different (c) mycolic acid wax ester antigens comprising different chain lengths.

Suitably the system comprises:
(a1) a trehalose monomycolate antigen comprising an alpha mycolic acid residue;
(a4) a trehalose monomycolate antigen comprising a keto mycolic acid residue;
(c1) a mycolic acid wax ester antigen; and
(c2) a mycolic acid wax ester antigen comprising a different chain length to the mycolic acid wax ester antigen of (c1).

Preferably it further comprises:
(d) a glucose monomycolate antigen.

The system may comprise more than one different (d) glucose monomycolate antigen, for example comprising different mycolic acid residues or different chain lengths. Suitably the more than one different (d) glucose monomycolate antigens comprise different mycolic acid residues, for example selected from keto mycolic acids, alpha mycolic acids and methoxy mycolic acids.

Preferably the system further comprises one or more of the following antigens:
(e) keto mycolic acids
(f) alpha mycolic acids;
(g) methoxy mycolic acids; and
(i) an arabinose mycolate antigen.

Preferably the system further comprises a keto mycolic acid, an alpha mycolic acid and a methoxy mycolic acid.

In some embodiments the system further comprises:
(h) an epoxy mycolic acid.

In one embodiment the system further comprises:
(a) a trehalose monomycolate antigen;
(b) a trehalose dimycolate antigen;
(c) a wax ester antigen;
(d) a glucose monomycolate antigen;
(e) keto mycolic acids;
(f) alpha mycolic acids;
(g) methoxy mycolic acids;

(h) an epoxy mycolic acid; and
(i) an arabinose mycolate antigen.

In one embodiment the system comprises:
(a) a trehalose monomycolate antigen;
(b) a trehalose dimycolate antigen; and
(h) an epoxy mycolic acid.

Suitably the system comprises:
(a2) a trehalose monomycolate antigen comprising a methoxy mycolic acid residue;
(b1) a trehalose dimycolate antigen comprising two alpha mycolic acid residues, suitably identical alpha mycolic acid residues;
(b3) a trehalose dimycolate antigen comprising two methoxy mycolic acid residues, suitably identical methoxy mycolic acid residues;
(b5) a natural human trehalose dimycolate antigen;
(b6) a natural bovine trehalose dimycolate antigen; and
(h) an epoxy mycolic acid.

In one embodiment the system comprises at least one (b) trehalose dimycolate antigen and at least one (i) arabinose mycolate antigen. Suitably the system comprises at least two different (i) arabinose mycolate antigens. Suitably the system comprises one (b) trehalose dimycolate antigen and two different (i) arabinose mycolate antigens.

Suitably the system comprises:
(b2) a trehalose dimycolate antigen comprising two keto mycolic acid residues, suitably identical keto mycolic acid residues;
(i1) an arabinose mycolate antigen comprising two alpha mycolic acid residues, suitably identical alpha mycolic acid residues; and
(i2) an arabinose mycolate antigen comprising two methoxy mycolic acid residues, suitably identical methoxy mycolic acid residues.

The system may comprise antigens that are obtained from mixtures of natural sources and thus contain a mixture of compounds.

Preferably at least two antigens are synthetically prepared antigens that are at least 90%, preferably at least 95% pure. More preferably the system comprises at least three, suitably at least 4, for example at least 5 or at least 6 synthetically prepared antigens that are at least 90%, preferably at least 95% pure.

In some embodiments the system may comprise one or more further antigens which are not mycolic-acid derived antigens.

In some embodiments the system comprises an adjuvant compound which enhances the binding of the biomarker with the antigen.

In some embodiments wherein the system comprises a substrate which carries the at least two different mycolic-acid derived antigens at different positions on the substrate, the substrate may at each position carry an adjuvant compound which enhances the binding of the biomarker with the antigen.

Step (a) may involve providing a substrate which carries an antigen.

Any suitable substrate may be used. For example the substrate may be a multiwell plate, typically made of polystyrene of the type commonly used in ELISA (enzyme-linked immunosorbent assay) assays. Multiwell plates of this type are known to the person skilled in the art. In such embodiments the antigens are suitably immobilised on the substance by conventional means. Suitably the at least two different mycolic-acid derived antigens are located, on the substrate, in different wells of a multiwell plate or are located on substrates in different multiwell plates, in an ELISA assay or assays.

In some preferred embodiments the substrate is a porous substrate.

The porous substrate may be any material which allows another medium to pass through it. Suitably the porous substrate allows liquid compositions and semi-solid or viscous liquid compositions (for example gels and pastes) to pass through.

Any suitable porous substrate may be used. Suitably the porous substrate is a woven material. Preferably the porous substrate is a cellulosic material.

The porous material carries an antigen. The antigen may be carried within the porous material or on the surface of the porous surface.

The substrate may be a gel.

Preferably the antigen forms a chemical interaction with the surface of the substrate. This may involve a polar interaction, for example dipole-dipole interactions or hydrogen bonding; or a non-polar interaction, for example Van der Waals forces.

In some preferred embodiments the antigen forms hydrogen bonds with functional groups at the surface of the substrate.

To prepare the substrate the antigen may be directly applied to the substrate.

In some preferred embodiments in which the substrate is a cellulosic material, a solution or suspension of the antigen may be applied to the substrate and the solvent allowed to evaporate. Without wishing to be bound by theory it is believed that hydrogen bonds form between the mycolic motif and/or residues in the sugar or glycerol residue of an ester and hydroxy groups of the cellulose.

Suitably the antigen is dissolved in a solvent. This may be an organic solvent, for example a mixture of hexanes; or an aqueous solvent, for example a buffer. The solution of antigen is suitably applied to the substrate and the solvent is then allowed to evaporate.

Suitably a small spot of antigen is applied to the substrate at each different position.

Areas of the substrate which do not contain an antigen spot or spots may be "blocked", for example an impermeable coating may be applied to the surface of the substrate in these regions.

In step (b) of the method of the present invention a sample obtained from an individual is introduced into the system and into contact with each of the at least two different mycolic-acid derived antigens. For the avoidance of doubt the sample is collected from the individual prior to carrying out the method of the present invention which is an in vitro method.

Any suitable sample may be tested using the present invention. Suitably the sample is selected from serum, blood, saliva, urine or sputum. In some embodiments the sample is blood. It may be serum.

The sample may contain a biomarker which becomes bound to or interacts with the antigen in the system, for example antigens carried on a substrate.

The sample may be directly contacted with the system or it may be diluted, filtered or otherwise purified prior to contact with the system. Suitable diluents, filtration methods and purification techniques will be known to the person skilled in the art.

The sample is suitably contacted with the system as a liquid or semi-liquid composition. Preferably it is a liquid composition.

In some embodiments the sample is diluted before contacting with the system. It may be diluted with an aqueous composition, suitably an aqueous buffer. Preferably it is diluted with an aqueous buffer having a pH of 6 to 8, preferably about 7. A casein buffer is especially preferred.

In some embodiments wherein the system comprises a substrate which carries the at least two different mycolic-acid derived antigens at different positions on the substrate, the substrate may be immersed in the sample or a composition comprising the sample.

In some embodiments the sample or a composition comprising the sample may be passed over the surface of the substrate.

In some embodiments in which the substrate is a porous substrate, the sample or a composition comprising the sample is contacted with a surface of the substrate and allowed to pass through the substrate.

In such embodiments the substrate may suitably be a sheet material. The sample or a composition comprising the sample may pass from one edge of the substrate to the opposite edge or may be contacted with a face of the substrate and pass through the substrate to the opposite face.

The sample or a composition comprising the sample may be contacted with the entire area of the substrate or a portion of the substrate, suitably the portion which carries the antigen.

Step (c) of the method of the present invention involves detecting the presence or absence of the binding of a biomarker in the sample with each antigen in the system, for example detecting the presence or absence of the binding of a biomarker in the sample with each antigen at each position on the substrate. Detection of the presence or absence of binding of each antigen may be carried out by any suitable means. Such means will be known to the person skilled in the art and include, for example by measuring the weight of the thickness of the components on the substrate.

In some preferred embodiments wherein the system comprises a substrate which carries the at least two different mycolic-acid derived antigens at different positions on the substrate, step (c) involves the steps:
  (i) contacting the substrate with a composition comprising a secondary antibody; and
  (ii) observing the substrate at each position.

Any antibody or antibody conjugate which interacts with the biomarker may be used as the secondary antibody. Preferred secondary antibodies include Immunoglobulin G and Immunoglobulin M.

In some embodiments the secondary antibody is linked to an enzyme via bio-conjugation. Such secondary antibodies are well known to the person skilled in the art and are, for example, commonly used in ELISA assays.

In some preferred embodiments step (c) involves contacting the system with a composition comprising colloidal gold particles wherein the colloidal gold particles carry a secondary antibody.

The composition comprising colloidal gold particles is preferably an aqueous suspension of gold nanoparticles.

Suitably the nanoparticles have an average size of from 1 to 200 nm, preferably from 5 to 150 nm, suitably from 10 to 100 nm, suitably from 20 to 80 nm, for example about 40 nm.

The composition may comprise one or more further ingredients for example cosolvents, preservatives or buffering agents.

Preferably the composition comprises a buffer. Preferably the composition has a pH of from 5 to 9, preferably from 6 to 8, for example about 7. In some especially preferred embodiments the composition comprises a casein buffer.

Suitably the nanoparticles of gold carry a secondary antibody on their surface.

The antibody suitably forms an interaction with the surface of the gold nanoparticles.

In some preferred embodiments the gold nanoparticles are coated with a composition which promotes interaction with the secondary antibody. Preferably the gold particles are coated with a polymer. Suitable polymers are able to stabilise the gold particles and covalently bind antibodies.

Suitably there is one or more washing steps between step (c)(i) and step (c)(ii).

In embodiments in which the substrate is contacted with a composition comprising colloidal gold particles the substrate is suitably washed after the substrate is contacted with the composition comprising colloidal gold particles. Preferably it is washed with a composition comprising a buffer. Preferably it is washed with a composition of pH 6 to 8, suitably about 7. An aqueous composition comprising a casein buffer is especially preferred.

Step (ii) involves observing the substrate at each position.

Each antigen may be able to bind with the same or a different biomarker.

Suitably in some embodiments a colour change in the region of the substrate which carries an antigen is observed when the biomarker is present in the sample. If the biomarker is absent no colour change is observed.

Thus in preferred embodiments a positive sample in which a biomarker has bound with a particular antigen causes a colour change and a negative sample in which there is no binding causes no colour change.

Step (ii) involves observing the substrate at each position at which different antigens are located.

Rapid diagnosis of mycobacterial diseases is known to be very difficult.

By measuring the interaction with more than one antigen, the present invention allows a greater degree of sensitivity and specificity to be achieved.

The inventors have surprisingly found that using a combination of different mycolic acid derived antigens, which provides a combination of different antibody responses, allows a much more accurate and reliable diagnosis. These results can also be achieved quickly and cheaply.

Suitably in the method of the present invention the presence or absence of a colour change at two or more different positions on the substrate in combination leads to the determination of whether or not an individual is infected with a mycobacterial disease.

The use of highly purified synthetic antigens as single compounds is particularly advantageous as this ensures a high degree of sensitivity and specificity. Particular combinations of antigens can be selected to distinguish between different mycobacterial diseases.

The present invention may provide improved distinction between latent and active *tuberculosis* and improved detection in patients who are co-infected with HIV.

In some embodiments step (ii) may involve quantitatively measuring the colour change at each position on the substrate. Quantitative analysis of this type may also help determine the severity of infection with a mycobacterial disease.

Step (ii) may also involve measuring a response change, for example a colour change, over time. This information may be useful in determining the type or extent of infection with a mycobacterial disease.

However in preferred embodiments, step (ii) may involve simply visually observing the presence or absence of a colour change to provide a qualitative assessment at each position on the substrate.

In the method of the present invention when the sample is contacted with the substrate in step (b), if the biomarker is present it interacts with the antigen carried on the substrate and is thus "tethered" to the surface of the substrate.

If no biomarker is present no interaction occurs with the antigen and the biomarker is not present at the surface of the substrate.

In step (c) (i) the substrate maybe contacted with a composition comprising colloidal gold particles which carries a secondary antibody or an enzyme-linked secondary antibody. If following step (b) the biomarker is carried on the surface of the substrate, the secondary antibody interacts with the biomarker and tethers the gold particles to the substrate. If no biomarker is carried on the surface of the substrate then the secondary antibody and appendent gold particles or enzyme pass through the substrate.

The gold particles have a red colour. Thus when a biomarker is present the region of the substrate which carries the antigen is red at the end of step (i). If no biomarker is present no colouration of the substrate is observed.

When the secondary antibody is linked to an enzyme in an ELISA type assay the method may suitably include a step of adding a composition comprising a substrate. The substrate suitably undergoes a colour change upon reaction with the enzyme indicating the presence of the enzyme and thus the secondary antibody and the biomarker. Suitable enzyme compositions are commonly used in ELISA assays and will be known to the person skilled in the art.

A particular advantage of the present invention is that it enables a very quick, simple test to be carried out to determine whether or not a particular sample contains a biomarker. Suitably it is used to determine whether or not the sample contains a biomarker indicative of exposure to mycobacteria, for example an antibody indicative of infection with or exposure to a mycobacterial disease. The method of the present invention may be carried out at remote locations, for example where there is no or limited access to hospitals, clinics, laboratories or specialist services. The combination of colour changes provides an immediate or almost immediate indication of whether the provider of the sample is infected with a mycobacterial disease.

The method of the present invention may be carried out using traditional ELISA methodology. Such methods are well known to the person skilled in the art and commonly known variations are within the scope of the invention.

The present invention may thus provide the use of two or more mycolic acid derived antigens in an ELISA assay to determine whether an individual is infected with a mycobacterial disease. Preferred features of this use are as defined in relation to the method of the first aspect.

In some preferred embodiments the method of the first aspect of the present invention comprises the steps of:
 (a) providing a porous substrate which carries at least two mycolic-acid derived antigens at different positions;
 (b) contacting the substrate with the sample; and
 (c) (i) contacting the substrate with a composition comprising colloidal gold particles, wherein the colloidal gold particles carry a secondary antibody; and
   (ii) observing the substrate at the two or more different positions.

Suitably steps (a), (b) and (c) are carried out in the order (a) followed by (b) followed by (c).

Features of this preferred method are as previously defined herein.

Suitably the porous substrate is a cellulosic substrate. Suitably the composition comprising colloidal gold particles is an aqueous suspension of gold nanoparticles.

The present invention provides a quick, reliable and accurate method by which it is possible to determine whether an individual is infected with a mycobacterial disease.

Step (c) preferably involves observing or measuring a colour change on the substrate. The results may be interpreted in a number of ways. In some embodiments a simple presence or absence of a colour change at a number of positions may be used to give a diagnosis. Thus the presence of three or four or more spots of colour on the device may be used to determine if the individual has the disease or not.

In some embodiments the colour change at multiple positions can be measured quantitatively. This could be carried out by a portable device, for example a mobile telephone. The quantitative data for each position can be stored electronically and analysed. Statistical analysis may be performed on these measurements and comparisons made with earlier results to determine the likelihood that an individual is infected.

For example a statistical algorithm could be used to assign a probability that any one sample is positive or negative for infection with a particular mycobacterial disease. Alternatively a principle co-ordinate analysis may be performed to arrange a number of results into groups, for example into groups which are either positive or negative for a particular mycobacterial disease, on a two-dimensional plot. Whether a subsequent sample result is positive or negative can then be determined using the result's position on the plot.

According to a second aspect of the present invention there is provided a kit for determining the presence or absence of a biomarker in a sample, the kit comprising:
 (x) a system which comprises two or more different mycolic-acid derived antigens; and
 (y) a composition comprising a secondary antibody.

Suitably the kit of this second aspect comprises:
 (x) a substrate which carries two or more different mycolic-acid derived antigens at different positions; and
 (y) a composition comprising a secondary antibody.

Preferred features of the second aspect are as defined in relation to the first aspect and features described in relation to the second aspect may also apply to the first aspect.

As described above the substrate may be a multiwell plate as commonly used in an ELISA assay and the composition comprising a secondary antibody may comprise an enzyme linked secondary antibody. In such embodiments the kit may further comprise a composition comprising a substrate for the enzyme. As will be understood by the skilled person the substrate for the enzyme is a small molecule with which the enzyme reacts and is distinct from the substrate previously defined herein which is a carrier for the antigens. The substrate for the enzyme may be a colorimetric substrate.

As previously described herein, in some preferred embodiments the substrate is a porous material, preferably a porous sheet material, for example a cellulosic material. In such embodiments the composition comprising the secondary antibody is suitably a composition comprising particles of colloidal gold particles wherein the colloidal gold particles carry a secondary antibody on their surface.

In the kit of the second aspect the substrate is preferably located within a suitable housing.

Preferably the substrate is positioned within the housing so as to enable the sample to contact the substrate.

Suitably the housing includes an aperture to enable the sample to contact the substrate in the region which carries the antigens.

In some preferred embodiments in which the substrate is porous it is positioned within the housing to enable the sample to pass through from one side of the substrate to the other.

The housing may further comprise a chamber to collect the sample and other compositions after they pass through the substrate. The chamber may include an absorbent material to soak up the excess sample, excess secondary antibody composition and/or any washing compositions.

The housing may be made from any suitable material. Preferably it is a plastic housing.

The absorbent material is preferably a sponge-like material.

According to a third aspect of the present invention there is provided a device comprising a housing and a system; wherein the system comprises at least two mycolic-acid derived antigens and is located within the housing.

Suitably the system comprises a substrate which carries the at least two different mycolic-acid derived antigens at different positions on the substrate.

Suitably the system comprises from 6 to 12 different mycolic-acid derived antigens, the different mycolic-acid derived antigens being selected from:

(i) mycolic acids and their esters obtained from natural sources;
(ii) synthetically prepared mycolic acids;
(iii) salts of mycolic acids;
(iv) esters of mycolic acids (i) and/or (ii);
(v) sulfur-containing mycolic acid compounds and/or salts or esters thereof;
(vi) simple structural analogues of mycolic acids and/or salts or esters thereof; and
(vii) mycolic acid wax esters and/or salts or esters thereof.

Suitably the device according to this third aspect comprises a housing and a substrate; wherein the substrate carries at least two mycolic-acid derived antigens at different positions and is located within the housing.

Suitably each antigen is selected from mycolic acids, wax esters analogous to mycolic acids, wax esters and salts and esters thereof.

Preferred features of the device of the third aspect are as defined in relation to the first and second aspects. The kit of the second aspect preferably comprises a device of the third aspect and the composition comprising a secondary antibody may suitably comprise a composition comprising colloidal gold particles which carry a secondary antibody on their surface.

When used to analyse known samples of sera from individuals some of whom had been infected with *M. tuberculosis*, the method of the present invention was found to provide a faster and more accurate method of discrimination between positive and negative samples compared with using standard methods of the prior art. The method of the present invention is also more suitable for point of care use than prior art methods, for example in environments with limited access to hospitals and laboratories.

Embodiments of the invention which use a porous substrate and a secondary antibody carried on colloidal gold particles are particularly suitable for use in remote locations.

When the present invention is used to test for disease antibodies indicative of infection with a mycobacterial disease it can provide results very quickly, with good accuracy and at relatively low cost. It therefore provides significant advantages over the prior art.

The present inventors have found that by measuring the interaction of biomarkers in a sample with more than one antigen simultaneously, for example in a single system, the accuracy of the diagnosis is greatly increased. The present invention may be used in a number of different applications.

In some embodiments the present invention may be used to determine whether an individual is infected with *M. tuberculosis*. In such embodiments the individual is suitably a human. The invention may enable a quick and accurate diagnosis of infection with *tuberculosis* allowing an infected patient to receive effective treatment much more quickly. The method of the invention has also been found to provide accurate diagnosis even in cases where patients are co-infected with HIV. The invention is also able to discriminate between infection with *M. tuberculosis* and other mycobacteria, for example *Mycobacterium avium* in humans.

The present invention can also be used to effectively diagnosis infection with *tuberculosis* in cattle.

The invention may be used to distinguish between cattle with active *tuberculosis*, young uninfected cattle and cattle that have been vaccinated. This is particularly advantageous as methods of the prior art have not been able to effectively distinguish vaccinated animals resulting in poor uptake of the vaccine.

The present invention may also provide a method of detecting infection with other mycobacterial diseases. Suitably the method of the present invention may be used to determine whether an individual is infected with Johne's disease.

In such embodiments the individual is suitably a ruminant, preferably a cow.

Johne's disease is a serious disease caused by infection with *Mycobacterium avium paratuberculosis*. The bacteria can lie dormant in animals for many years before symptoms appear but can be easily transmitted between animals in a herd. It is often difficult using diagnosis methods of the prior art to distinguish between infection with *Mycobacterium tuberculosis* which causes bovine *tuberculosis* and infection with *Mycobacterium avium paratuberculosis* which causes Johne's disease.

The present inventors have found that improved detection of Johne's disease can be achieved when using a mycolic acid wax ester or an ester thereof as an antigen.

Thus the present invention provides a method of determining whether an individual is infected with mycobacteria, the method comprising:

(a) providing a system which comprises at least two different mycolic-acid derived antigens;
(b) introducing a sample obtained from the individual into the system and into contact with each of the at least two different mycolic-acid derived antigens; and
(c) detecting the presence or absence of the binding of a biomarker in the sample with each antigen in the system;

wherein at least one of the mycolic acid derived antigens is a wax ester or a derivative thereof.

The present invention may provide a method of determining whether an individual is infected with *Mycobacterium avium paratuberculosis*, the method comprising:

(a) providing a substrate which carries at least two different mycolic-acid derived antigens at different positions;
(b) contacting the substrate with a sample obtained from the individual; and (c) detecting the presence or absence of the binding of a biomarker in the sample with each antigen at each position on the substrate;
wherein at least one of the mycolic acid derived antigens is a wax ester or a derivative thereof.

Suitable wax ester derivatives for use as antigens are esters and salts. Sugar esters are preferred, especially trehalose esters.

Suitably in the method of determining whether an individual is infected with *M. avium paratuberculosis*, step (a) involves providing a system which comprises a first antigen that is a wax ester or a derivative thereof and a second antigen that is selected from a trehalose monomycolate and a trehalose dimycolate. Preferably the system comprises more than 2 antigens, suitably at least 4 antigens, preferably from 4 to 16, for example from 6 to 10 antigens.

Suitably the method is a method of distinguishing between infection with *M. avium* and infection with *M. tuberculosis*.

Because the kit and method of the present invention provide a result in a quick and relatively inexpensive manner they may be used in a method of public health screening.

The present invention may be used to screen large populations to determine the levels of levels of antibody response and therefore exposure to mycobacteria and other organisms producing mycolic acids. This may include screening for latent mycobacterial infection.

It is common for certain populations to include high numbers of individuals who are carriers of latent mycobacteria. These are individuals who are infected with the bacteria but do not have any active disease. However in populations in which infection with latent mycobacteria is high, there is an increase in the incidence of mycobacterial diseases. Identifying populations or groups of individuals who are infected with latent mycobacteria can help predict where outbreaks of disease are likely. Public health officials can then provide increased monitoring of these populations and take steps to reduce the likelihood of serious disease outbreaks occurring.

The present invention could thus provide a device to allow individuals to check on a routine basis that they have normal immune responses. For example an over the counter device could be provided to allow at risk groups such as farmers, abattoir workers, vets or other people working with animals (and their animals) to identify abnormal immune responses to lipid antigens and seek appropriate medical advice as early as possible. Likewise the device may allow employers to routinely check whether their workforce have abnormal immune responses to lipid antigens which could be indicative of exposure to or infection with mycobacteria.

According to a fourth aspect of the present invention there is provided a composition comprising at least two different mycolic-acid derived antigens.

Preferably the composition is suitable for use in a method, kit or device of the first, second and third aspects. The composition of this fourth aspect may comprise any of the suitable or preferred antigens described in relation to the first, second and third aspects.

Suitably the at least two different mycolic-acid derived antigens comprise from 6 to 12 different mycolic-acid derived antigens selected from:
(i) mycolic acids and their esters obtained from natural sources;
(ii) synthetically prepared mycolic acids;
(iii) salts of mycolic acids;
(iv) esters of mycolic acids (i) and/or (ii);
(v) sulfur-containing mycolic acid compounds and/or salts or esters thereof;
(vi) simple structural analogues of mycolic acids and/or salts or esters thereof; and
(vii) mycolic acid wax esters and/or salts or esters thereof.

Suitably the at least two different mycolic-acid derived antigens comprise:
(a) a trehalose monomycolate antigen; and/or
(b) a trehalose dimycolate antigen; and/or
(c) a mycolic acid wax ester antigen; and/or
(d) a glucose monomycolate antigen; and/or
(i) an arabinose mycolate antigen.

The invention will now be further described with reference to FIGS. 1 and 2.

Figure 1:
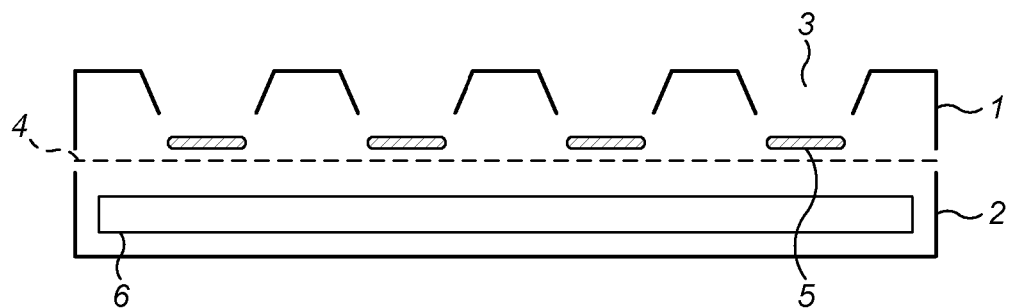
FIG. 1 shows a cross-sectional view of a device of the third aspect of the present invention.
Figure 2:
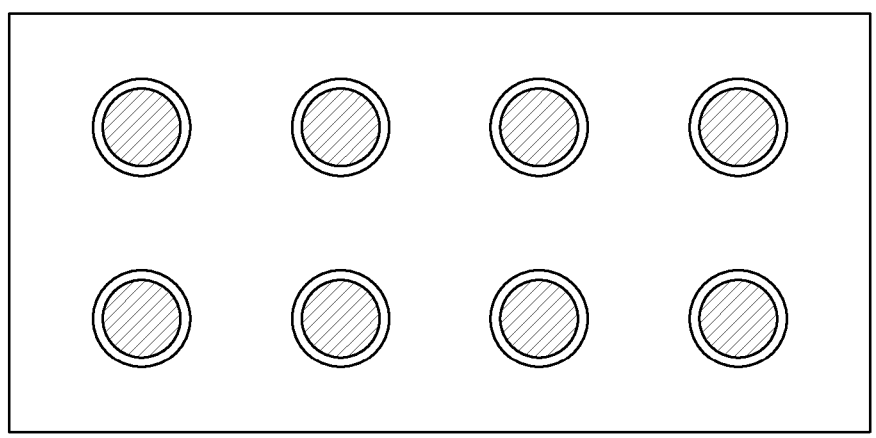
FIG. 2 shows a schematic top view of the device of FIG. 1.

The device of FIGS. 1 and 2 comprises a plastic housing having an upper portion 1 and a lower portion 2. The upper portion includes a plurality of apertures 3. The sides of the apertures are shaped to direct liquid through the apertures. A porous substrate 4 is located within the housing. A plurality of antigens are provided on the substrate in the region below the apertures 5. A sponge 6 is provided below the substrate.

The invention will now be further described with reference to the following non-limiting examples.

EXAMPLE 1

ELISA Test Method

ELISAs were carried out on 96-well flat-bottomed polystyrene micro-plates. Antigens were dissolved in hexane to give an antigen solution of concentration 15 µg/ml. 50 µl of this solution was added to each well, and the solvent was left to evaporate at room temperature. Control wells were coated with hexane (50 µl/well) only. Blocking was done by adding 400 µl of 0.5% casein/PBS buffer (pH=7.4) to each well, and the plates were incubated at 25° C. for 30 minutes. The buffer was aspirated and any excess buffer was flicked out until the plates were dry. Serum (1 in 20 dilution in casein/PBS buffer) (50 µl/well) was added and incubated at 25° C. for 1 hour. The plates were washed with 400 µl casein/PBS buffer 3 times using an automatic washer, and any excess buffer was flicked out onto a paper towel until dry. Secondary antibody (anti-human IgG (Fc specific) peroxidise conjugated antibody produced in goat (Aldrich) diluted to a concentration of 1:2000 in casein/PBS buffer, 50 µl/well) was added, and incubated at 25° C. for 30 minutes. The plates were again washed 3 times with 400 µl casein/PBS buffer using an automatic washer, and any excess buffer was again flicked out. OPD substrate (o-phenylenediamine (1 mg/ml) and $H_2O_2$ (0.8 mg/ml) in 0.1 M citrate buffer, 50 µl/well) was then added, and the plates were incubated for a further 30 minutes at 25° C. The colour reaction was terminated by adding 2.5 M $H_2SO_4$ (50 µl/well), and the absorbance was read at 492 nm. All numbers give in tables of ELISA results are optical density readings.

EXAMPLE 2

Identification of bovine TB Infected Cattle Serum and Distinction from that of Vaccinated Animals The serum from two sets of animals was examined in ELISA using seven different mycolic acid derived antigens. These included a natural human trehalose dimycolate and a natural bovine trehalose dimycolate. The other antigens were the following synthetically prepared compounds:

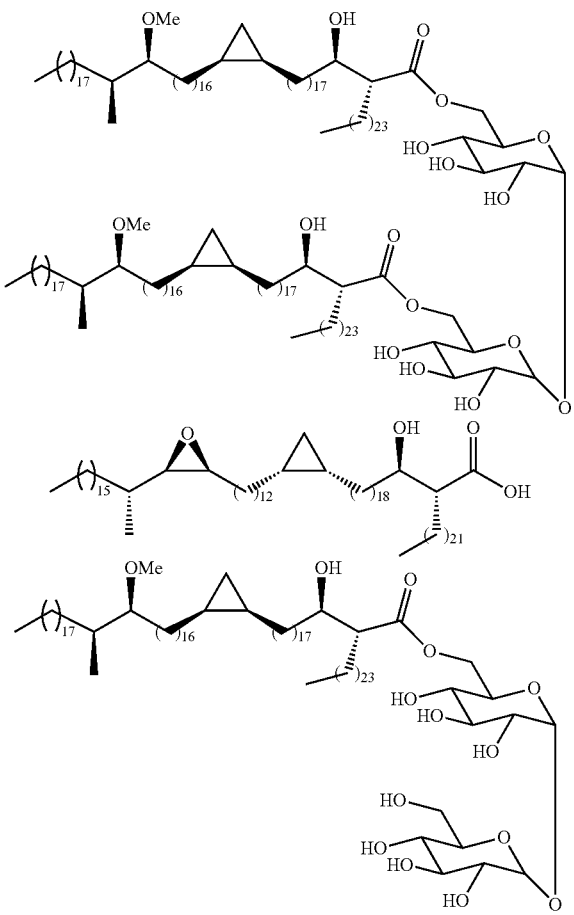

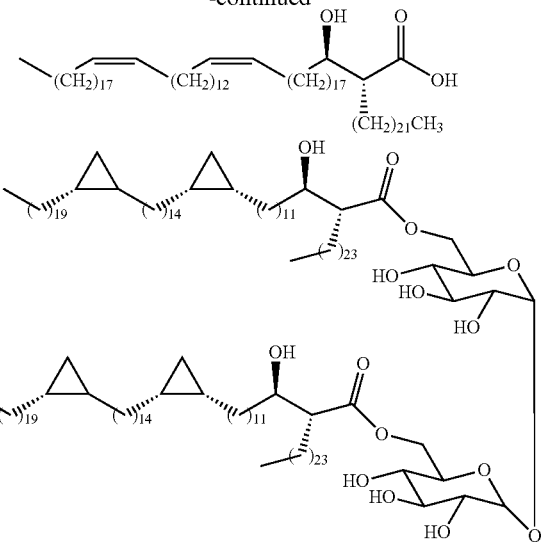

Figure 3:
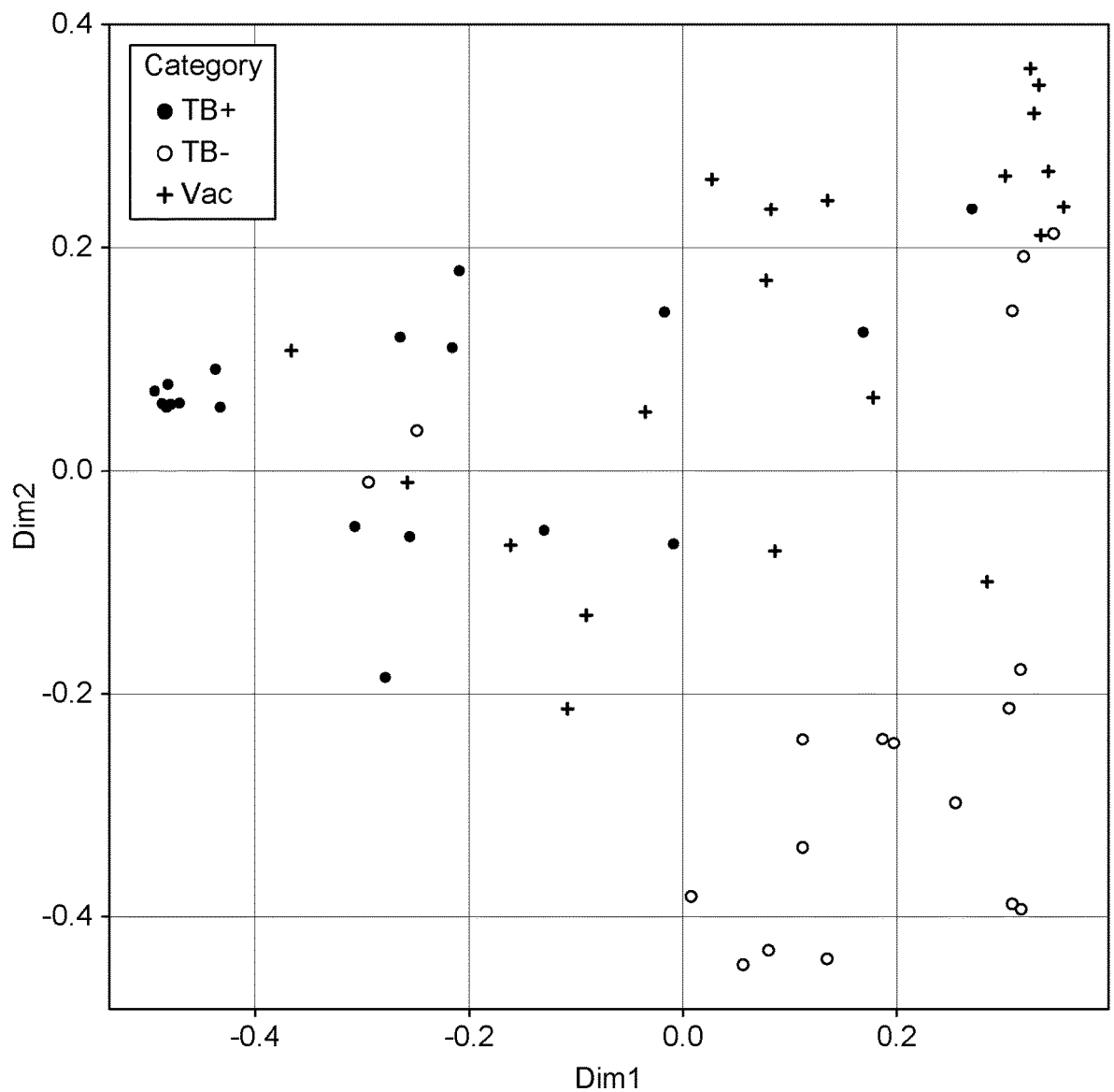
FIG. 3 shows a principal co-ordinate analysis plot of the data from Example 2.

The samples labelled as TB+ were from cattle identified as being naturally infected with bovine TB. The samples labelled as TB− were from non-infected cattle. Samples labelled as vaccinated were from uninfected but vaccinated cattle. The 7 different antigens showed variable sensitivity/specificity combinations. Statistical combination of the data for all the antigens using principal co-ordinate analysis provided the distribution pattern in FIG. 3, in which the infected and non-infected groups are separated at the left and bottom right of the plot and vaccinated samples in the top right of the plot, apart from a small number of intermediate samples. Each axis of the plot represents a combination of the results from multiple antigens using principle co-ordinate analysis.

EXAMPLE 3

A set of 64 samples of serum from patients attending a surgery with suspected TB (*tuberculosis*) in a high burden TB population was examined using ELISA. Samples 1-9 had been diagnosed as positive for infection with *tuberculosis* (TB+) on the basis of a range of assays including sputum smear and culture, samples 10-64 as negative for infection with *tuberculosis* (TB−). An ELISA assay was carried out with three synthetic antigens having the structures:

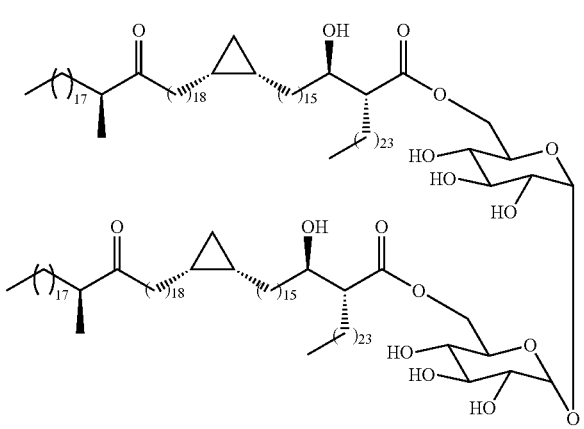

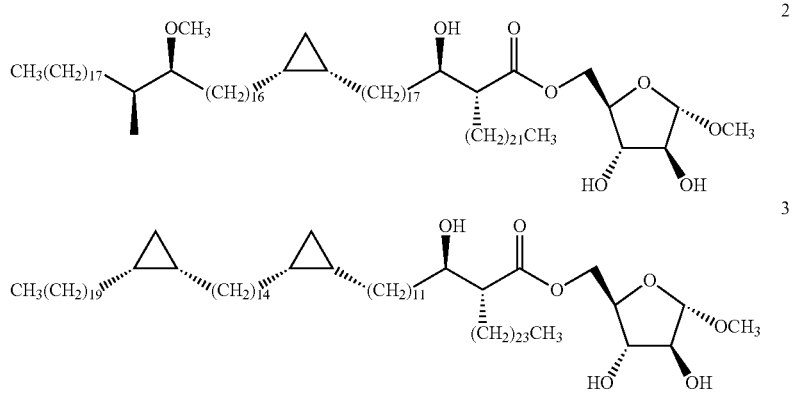

Cut-off values were set to identify all the positive samples, and the false positives were then identified as those above the cut-off for each antigen. Values above the cut-off are shown by * in Table 1. The sensitivity was found to be 100%. 53 of the 55 negatives were correctly identified giving a specificity of 96%.

TABLE 1

| Sample (diagnosis in brackets) | Antigens | | |
|---|---|---|---|
| | 1 | 2 | 3 |
| | Dilution of sample: | | |
| | 1 in 20 | 1 in 80 | 1 in 80 |
| 1 (TB+) | 2.95* | 0.42* | 0.74* |
| 2 (TB+) | 4.41* | 0.36* | 0.76* |
| 3 (TB+) | 3.66* | 0.77* | 0.99* |
| 4 (TB+) | 3.92* | 0.90* | 0.97* |
| 5 (TB+) | 3.31* | 0.38* | 0.99* |
| 6 (TB+) | 4.22* | 0.54* | 1.39* |
| 7 (TB+) | 3.55* | 1.15* | 1.97* |
| 8 (TB+) | 3.88* | 0.69* | 1.67* |
| 9 (TB+) | 1.31* | 0.56* | 1.09* |
| 10 (TB−) | 0.39 | 0.35 | 0.59 |
| 11 (TB−) | 0.71 | 0.45* | 0.92* |
| 12 (TB−) | 4.06* | 0.29 | 0.84* |
| 13 (TB−) | 0.64 | 0.34 | 0.60 |
| 14 (TB−) | 1.25 | 0.58* | 1.30* |
| 15 (TB−) | 0.60 | 0.37* | 0.64 |
| 16 (TB−) | 0.21 | 0.42* | 0.56 |
| 17 (TB−) | 1.54* | 0.47* | 0.81* |
| 18 (TB−) | 0.36 | 0.25 | 0.68 |
| 19 (TB−) | 1.17 | 0.31 | 0.71* |
| 20 (TB−) | 0.51 | 0.38* | 1.03* |
| 21 (TB−) | 0.55 | 0.35 | 0.61 |
| 22 (TB−) | 2.53* | 0.24 | 0.66 |
| 23 (TB−) | 0.33 | 0.35* | 0.81* |
| 24 (TB−) | 1.66* | 0.26 | 0.62 |
| 25 (TB−) | 0.19 | 0.18 | 0.21 |
| 26 (TB−) | 0.62 | 0.24 | 0.72* |
| 27 (TB−) | 0.55 | 0.33 | 0.61 |
| 28 (TB−) | 0.30 | 0.23 | 0.38 |
| 29 (TB−) | 0.31 | 0.29 | 0.41 |
| 30 (TB−) | 0.36 | 0.24 | 0.39 |
| 31 (TB−) | 0.45 | 0.30 | 0.51 |
| 32 (TB−) | 1.29 | 0.57* | 0.91* |
| 33 (TB−) | 0.52 | 0.46* | 0.42 |
| 34 (TB−) | 0.46 | 0.51* | 0.49 |
| 35 (TB−) | 0.39 | 0.26 | 0.38 |
| 36 (TB−) | 0.25 | 0.23 | 0.28 |
| 37 (TB−) | 1.32* | 0.41* | 0.55 |
| 38 (TB−) | 0.81 | 0.40* | 0.52 |
| 39 (TB−) | 0.27 | 0.31 | 0.35 |
| 40 (TB−) | 0.41 | 0.25 | 0.35 |
| 41 (TB−) | 0.23 | 0.33 | 0.66 |
| 42 (TB−) | 2.97* | 0.42* | 0.55 |
| 43 (TB−) | 0.50 | 0.29 | 0.30 |
| 44 (TB−) | 2.34* | 0.67* | 0.98* |
| 45 (TB−) | 0.74 | 0.35* | 0.43 |
| 46 (TB−) | 0.32 | 0.26 | 0.31 |
| 47 (TB−) | 0.55 | 0.41* | 0.56 |
| 48 (TB−) | 0.92 | 0.17 | 0.32 |
| 49 (TB−) | 0.49 | 0.25 | 0.51 |
| 50 (TB−) | 2.37* | 0.30 | 0.37 |
| 51 (TB−) | 1.66* | 0.18 | 0.21 |
| 52 (TB−) | 0.54 | 0.26 | 0.36 |
| 53 (TB−) | 0.87 | 0.25 | 0.26 |
| 54 (TB−) | 2.11* | 0.20 | 0.27 |
| 55 (TB−) | 0.39 | 0.22 | 0.27 |
| 56 (TB−) | 0.65 | 0.31 | 0.73* |
| 57 (TB−) | 1.39* | 0.29 | 0.37 |
| 58 (TB−) | 0.41 | 0.28 | 0.41 |
| 59 (TB−) | 1.11 | 0.25 | 0.45 |
| 60 (TB−) | 1.16 | 0.29 | 0.44 |
| 61 (TB−) | 0.63 | 0.34 | 0.41 |
| 62 (TB−) | 1.64* | 0.35* | 0.30 |
| 63 (TB−) | 0.48 | 0.22 | 0.25 |
| 64 (TB−) | 4.32* | 3.98* | 0.29 |
| Individual Sensitivity | 89 | 100 | 100 |
| Individual Specificity | 87 | 67 | 80 |

EXAMPLE 4

Use of the Method in Screening Samples Co-Infected with HIV

Figure 4:
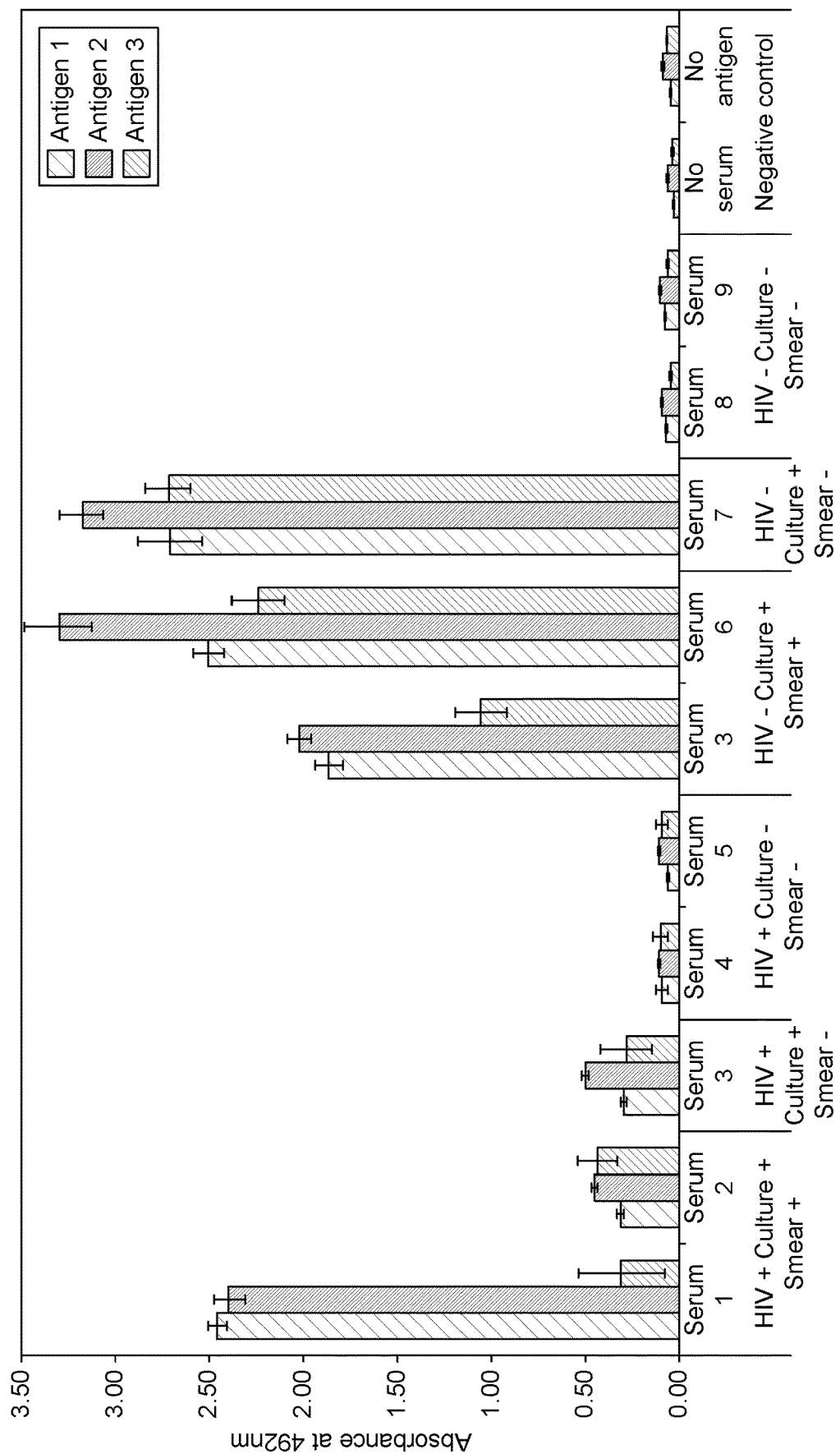
FIG. 4 shows a bar chart of the ELISA assay results described in Example 4.

The method has been shown to work in ELISA, using the method described above for human serum samples, with a range of different types of serum. Importantly, with the samples shown in the bar chart of FIG. 4, responses are seen with HIV+/TB+ serum (both culture+/smear+ and culture+/smear−) and with HIV−/TB+ culture+/smear− serum, against antigens 1-3 as described above.

EXAMPLE 5

An assay was carried out using ELISA with twelve cattle identified by standard tests as being Btb+ (positive for bovine *tuberculosis*) and 11 Btb−. A positive result in the current assay corresponds to four results above the cut-off for each antigen. A single false positive and no false negatives were observed giving a sensitivity of 100% and specificity of 91% (see Table 2).

TABLE 2

|  |  | Antigens | | | |
| --- | --- | --- | --- | --- | --- |
|  |  | 1 | 2 | 3 | 4 |
| Naturally infected | 1 | 1.49* | 1.51* | 0.38* | 2.14* |
|  | 2 | 2.59* | 1.78* | 0.54* | 1.5* |
|  | 3 | 1.85* | 1.86* | 1.24* | 1.58* |
|  | 4 | 2.51* | 0.58* | 1.82* | 0.49* |
|  | 5 | 0.68* | 0.48* | 1.56* | 1.42* |
|  | 6 | 1.7* | 0.3* | 2.03* | 0.52* |
|  | 7 | 1.2* | 0.86* | 2.77* | 1.31* |
|  | 8 | 3.02* | 0.63* | 3.29* | 0.89* |
|  | 9 | 0.91* | 0.27* | 2.62* | 0.25* |
|  | 10 | 0.57* | 0.31* | 1.02* | 0.28* |
|  | 11 | 0.52* | 0.35* | 0.98* | 0.48* |
|  | 12 | 3.94* | 0.31* | 4.05* | 0.35* |
|  | 13 | 1.34* | 0.29* | 0.33 | 0.21 |
|  | 14 | 0.47 | 0.18 | 0.21 | 0.14 |
| Non infected | 15 | 0.65* | 0.25 | 0.47* | 0.18 |
|  | 16 | 0.47 | 0.3* | 0.32 | 0.25* |
|  | 16 | 0.6* | 0.2 | 0.87* | 0.28* |
|  | 18 | 0.43 | 0.49* | 1.03* | 0.62* |
|  | 19 | 0.5 | 0.27* | 0.62* | 1.21* |
|  | 20 | 0.79* | 0.26* | 0.96* | 0.57* |
|  | 21 | 0.33 | 0.35* | 0.45* | 0.65* |
|  | 22 | 0.76* | 0.23 | 0.74* | 0.21 |
|  | 23 | 0.35 | 0.62* | 0.67* | 1.13* |
| Cut-off for positive |  | >.5 | >.25 | >.35 | >.24 |

The antigens used had the following structures:

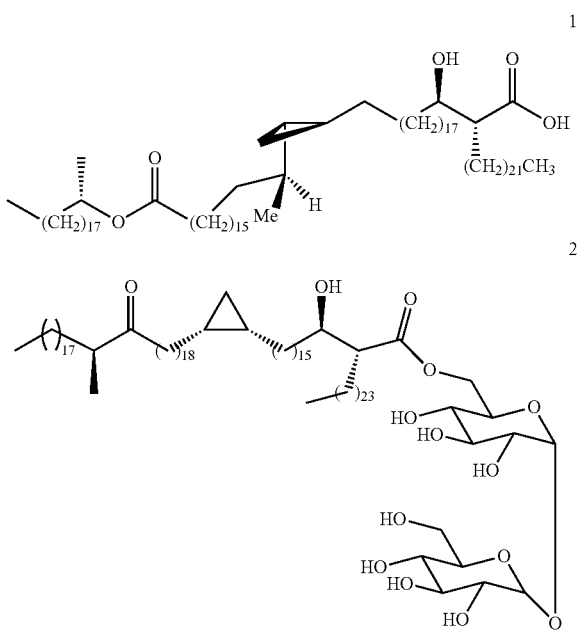

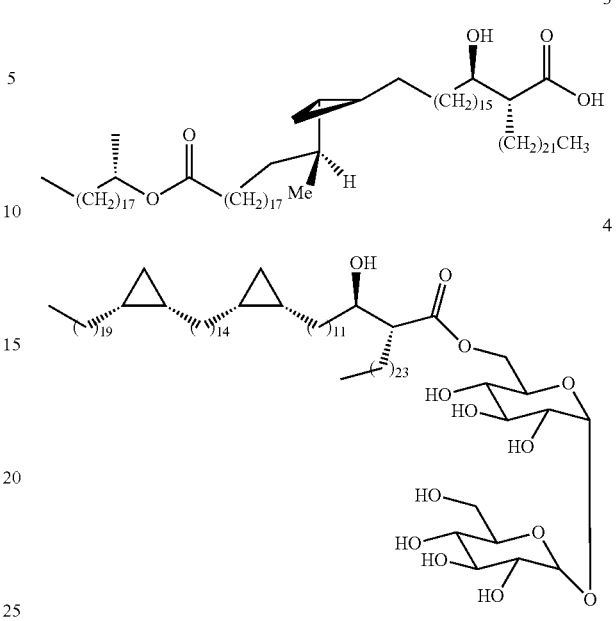

EXAMPLE 6

Quantitative Prediction of TB+ Status Based on Combination of ELISA Results for 8 Antigens—Single Probability Figure for TB or no TB 100 sera from TB indigenous countries were tested using a set of 8 antigens including synthetic TDM and TMM from various classes. The results were combined and analysed statistically to provide a quantitative measure of the likelihood that an individual sample was TB+ or TB−. A single number was obtained ranging from 1000 to 0, corresponding to the probability that any single sample was from a TB+ patient, with 1000 being the highest probability of a positive serum. The prediction was compared with the clinical diagnosis. Samples were all obtained from individuals presenting with the symptoms of active *tuberculosis* and were clinically diagnosed as having, or not having TB based of a range of assays.

The results were ranked in order of positive prediction. Samples 1-19 were all clinically diagnosed as TB+ and gave probabilities of 996-897 out of 1000 in the combined assay. Sample 20 was clinically TB− and gave a value of 882. Sample 21 was TB+ and gave a value of 801. Samples 22-25 were clinically TB− and gave values ranging from 797 to 761. Samples 26-29 were TB+ and gave values from 753 to 678. Samples 30 and 31 were TB− and gave values of 655 and 644. All other samples were clinically negative; the next four gave values of 612 to 551, all others values were below 400. By setting a cut off for positive diagnosis of 750 in the combined assay, a sensitivity of 100% and specificity of 92% was observed. The cut-off can be set to identify samples which require further examination. In this assay, neither previous TB in the patient providing the serum sample nor previous BCG vaccination interfered with the ELISA diagnosis.

EXAMPLE 7

Use of the Method of the Present Invention in Public Health Screening

The binding of synthetic antigens to antibodies in serum samples obtained from different groups from the normal population within Wales was examined in ELISA assays. In order to compare the results with those from other populations, the values were compared to average responses from two sets of samples provided by the World Health Organisation from a sample bank. These were taken from people who were referred to a clinic with some of the symptoms of *tuberculosis*; they are divided into two sets, those finally clinically diagnosed as having active TB, and those for whom the diagnosis was negative. These samples were all taken from countries with a high TB burden. This means that latent TB infection is common in such populations.

Antigens 1 to 7 were synthesised by known methods. Antigens 1 and 2 are trehalose di- and mono-mycolates (TDM and TMM) of an α-mycolic acid corresponding to the main chain lengths of such compounds in *M. tuberculosis*. Antigens 3-6 are the corresponding TDM and TMM for different stereochemistries of methoxy-mycolic acids, again corresponding to the major chain lengths in *M. tuberculosis*, while antigen 7 is a corresponding keto-mycolic acid. The antigens have the following structures:

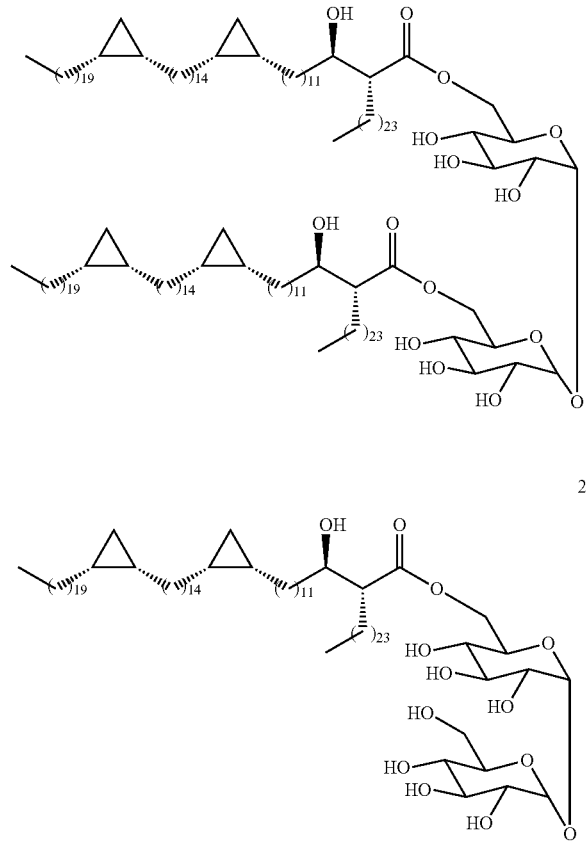

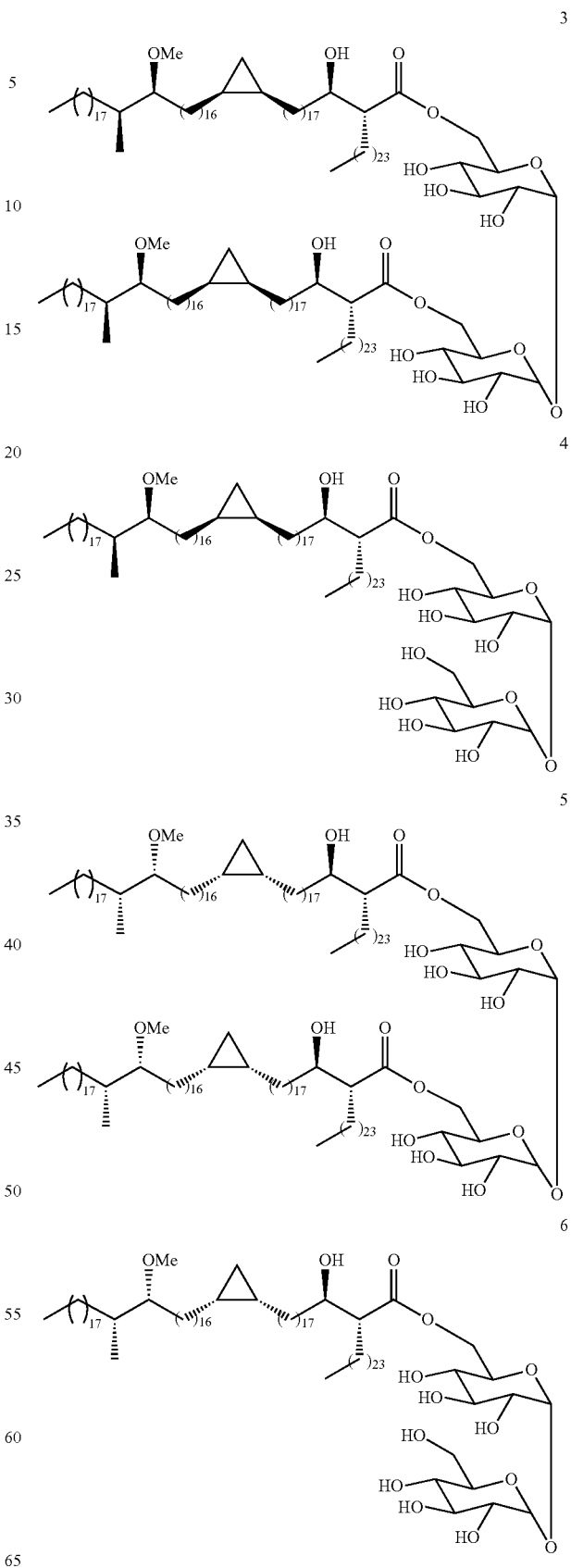

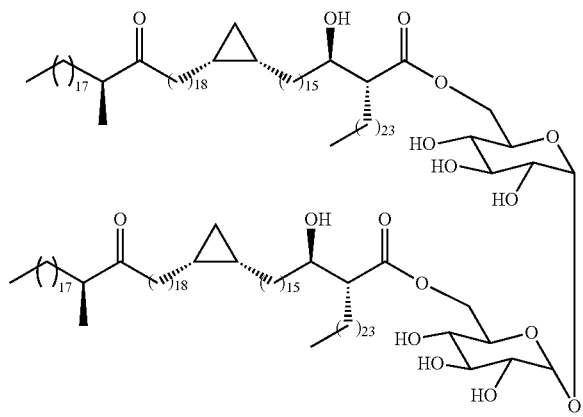

Serum samples were obtained from a sample bank collected initially for a study to detect the prevalence of *E. coli* in the normal Welsh population. The samples were used under an appropriate ethical approval. They were divided into four broad sets: i) those obtained from farmers (BF); ii) those obtained from abattoir workers fulfilling a number of job roles (BA); iii) samples from people living in rural Wales (BR); iv) samples from people living in urban Wales (BU). The results of the ELISA assays, carried out in triplicate are presented in Tables 3-6. show the average responses for each set of samples against seven different antigens, together with the total of those responses, compared to the corresponding figures for two sets of samples provided by the World Health Organisation. All of these samples were from individuals in high TB-burden populations having some of the symptoms of *tuberculosis*; those in the WHO+ set were diagnosed on the basis of a set of criteria including smear and culture to have the disease; those in the WHO− set were diagnosed as not having active disease.

TABLE 3

Average responses of serum samples in ELISA assay

| | Antigen | | | | | | | |
|---|---|---|---|---|---|---|---|---|
| | 1 | 2 | 3 | 4 | 5 | 6 | 7 | Total |
| WHO+ | 2.97 | 2.58 | 2.53 | 2.19 | 2.83 | 2.45 | 3.11 | 18.67 |
| WHO− | 1.39 | 1.36 | 0.99 | 0.96 | 0.99 | 0.96 | 1.00 | 7.65 |
| BF (farmers) | 1.03 | 0.80 | 0.64 | 0.59 | 0.79 | 0.71 | 1.12 | 5.68 |
| BR (rural) | 0.31 | 0.3 | 0.37 | 0.29 | 0.49 | 0.43 | 0.56 | 2.76 |
| BU (urban) | 0.65 | 0.63 | 0.43 | 0.36 | 0.53 | 0.46 | 0.8 | 3.87 |
| BA (abbatoir workers) | 0.64 | 0.65 | 0.34 | 0.32 | 0.54 | 0.5 | 0.51 | 3.52 |

Figure 5:
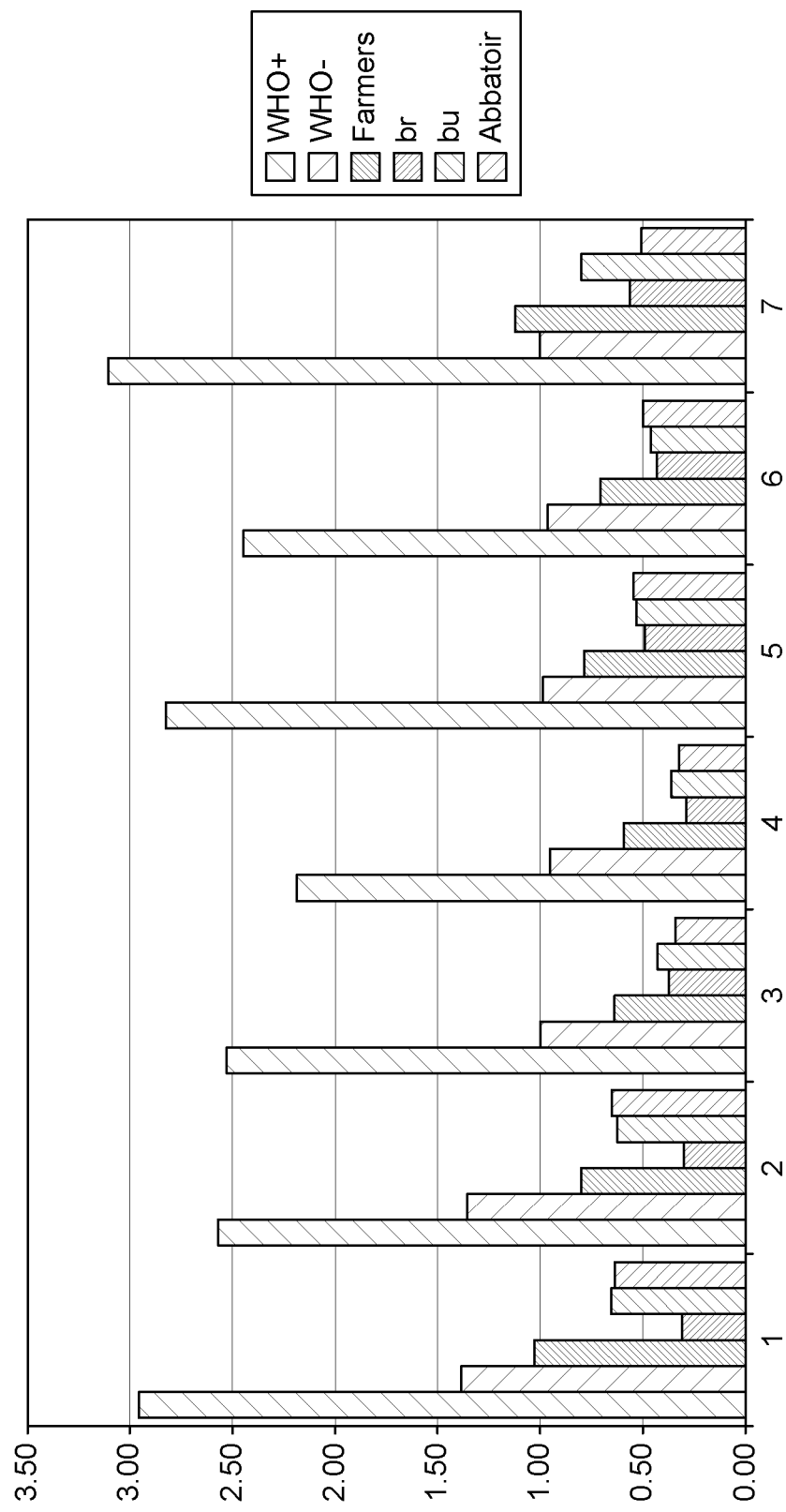
FIG. 5 shows a bar chart of the data from Table 3 described in Example 7.

These averages are presented graphically in the bar chart of FIG. 5.

It is clear from these results that the averages for all four sets of samples from a healthy population in this study were below those of the WHO TB-negative samples. Moreover, in many cases the averages were less than half those of this WHO set. It is also clear, however, that the figures for the 'farmers' set were considerably higher than those for the others, and in a number of cases close to the values of the TB− samples from high burden TB populations. An analysis of each set reveals further differences.

Table 4 shows the responses for a set of individuals living either in the town or the country, but who are not themselves farmers or working with animals as a profession. The boxes highlighted show those values which are above the average for the TB-negative WHO samples. It can be seen that, of these 55 samples, the number having above average WHO− negative values for individual antigens was small; the pattern of responses was also different even in these cases.

Table 4: Responses of BU (sample numbers in column 1, 45-63) and BR samples (column 1, 64-89) in the antigen antibody assay. Columns 2-8 represent the responses in the assay with antigens 1-7. Values marked with * are above the average for the WHO-negatives for a particular antigen.

TABLE 4

Responses of BU (sample numbers in column 1, 45-63) and BR samples (column 1, 64-89) in the antigen antibody assay. Columns 2-8 represent the responses in the assay with antigens 1-7. Values marked with * are above the average for the WHO-negatives for a particular antigen.

| | Antigen | | | | | | |
|---|---|---|---|---|---|---|---|
| | 1 | 2 | 3 | 4 | 5 | 6 | 7 |
| WHO + average | 2.97 | 2.58 | 2.53 | 2.19 | 2.83 | 2.45 | 3.11 |
| WHO − average | 1.39 | 1.36 | 0.99 | 0.96 | 0.99 | 0.96 | 1.00 |
| 45 | 0.33 | 0.28 | 0.22 | 0.20 | 0.39 | 0.33 | 0.22 |
| 46 | 0.29 | 0.29 | 0.24 | 0.25 | 0.41 | 0.36 | 0.49 |
| 47 | 0.29 | 0.60 | 0.31 | 0.41 | 0.48 | 0.31 | 0.52 |
| 48 | 0.25 | 0.21 | 0.37 | 0.19 | 0.38 | 0.29 | 0.50 |
| 49 | 0.21 | 0.18 | 0.23 | 0.18 | 0.24 | 0.21 | 0.30 |
| 50 | 0.31 | 0.32 | 0.41 | 0.35 | 0.53 | 0.41 | 0.58 |
| 51 | 0.27 | 0.20 | 0.17 | 0.10 | 0.29 | 0.16 | 0.83 |
| 52 | 0.55 | 0.56 | 0.47 | 0.44 | 0.65 | 0.64 | 1.08* |
| 53 | 0.47 | 0.50 | 0.63 | 0.35 | 0.63 | 0.57 | 1.03* |
| 54 | | | 0.50 | 0.23 | 0.72 | 0.45 | 0.83 |
| 55 | 0.28 | 0.29 | 0.26 | 0.20 | 0.30 | 0.26 | 0.27 |
| 56 | 0.29 | 0.25 | 0.30 | 0.24 | 0.35 | 0.28 | 0.34 |
| 57 | 0.50 | 0.32 | 0.43 | 0.32 | 0.70 | 0.43 | 0.70 |
| 58 | | | 0.59 | 0.50 | 0.52 | 0.72 | 0.76 |
| 59 | | | 0.51 | 0.54 | 0.56 | 0.79 | 0.60 |
| 60 | 0.44 | 0.32 | 0.24 | 0.27 | 0.56 | 0.49 | 0.63 |

TABLE 4-continued

Responses of BU (sample numbers in column 1, 45-63) and BR samples (column 1, 64-89) in the antigen antibody assay. Columns 2-8 represent the responses in the assay with antigens 1-7. Values marked with * are above the average for the WHO-negatives for a particular antigen.

|  | Antigen | | | | | | |
|---|---|---|---|---|---|---|---|
|  | 1 | 2 | 3 | 4 | 5 | 6 | 7 |
| 61 | 0.59 | 0.49 | 0.48 | 0.28 | 0.78 | 0.55 | 0.33 |
| 62 | 0.46 | 0.55 | 0.34 | 0.22 | 0.48 | 0.49 | 0.35 |
| 63 | 0.38 | 0.43 | 0.27 | 0.28 | 0.44 | 0.42 | 0.28 |
| Average | 0.31 | 0.30 | 0.37 | 0.29 | 0.49 | 0.43 | 0.56 |
| 64 | 0.16 | 0.28 | 0.12 | 0.32 | 0.16 | 0.33 | 0.24 |
| 65 | 0.29 | 0.23 | 0.18 | 0.17 | 0.16 | 0.17 | 0.21 |
| 66 | 0.33 | 0.39 | 0.23 | 0.30 | 0.26 | 0.31 | 0.28 |
| 67 | 0.21 | 0.24 | 0.21 | 0.19 | 0.28 | 0.23 | 0.32 |
| 68 | 0.56 | 0.42 | 0.39 | 0.28 | 0.50 | 0.31 | 0.78 |
| 69 | 0.40 | 0.41 | 0.24 | 0.21 | 0.20 | 0.17 | 0.30 |
| 70 | 0.55 | 0.50 | 0.32 | 0.34 | 0.54 | 0.52 | 0.71 |
| 71 | 0.25 | 0.28 | 0.20 | 0.19 | 0.23 | 0.18 | 0.24 |
| 7 | 0.47 | 0.96 | 0.88 | 0.46 | 1.93* | 0.52 | 2.09* |
| 73 | 0.21 | 0.24 | 0.16 | 0.13 | 0.26 | 0.26 | 0.32 |
| 74 | 2.64* | 1.23 | 0.81 | 0.70 | 1.51* | 0.75 | 1.97* |
| 75 | 0.25 | 0.58 | 0.31 | 0.33 | 0.51 | 0.51 | 0.53 |
| 76 | 1.20 | 1.03 | 0.97 | 0.58 | 0.81 | 0.78 | 1.73* |
| 77 | 0.30 | 0.36 | 0.25 | 0.22 | 0.37 | 0.26 | 0.54 |
| 78 | 0.42 | 1.06 | 0.48 | 0.61 | 0.72 | 1.15* | 0.51 |
| 79 | 1.51* | 1.04 | 0.92 | 0.66 | 1.25* | 1.10* | 2.21* |
| 80 | 0.84 | 0.78 | 0.54 | 0.46 | 0.71 | 0.66 | 1.28* |
| 81 | 0.33 | 0.78 | 0.12 | 0.41 | 0.48 | 0.64 | 0.57 |
| 82 | 0.29 | 0.32 | 0.30 | 0.22 | 0.35 | 0.32 | 0.45 |
| 83 | 1.33 | 1.63* | 0.70 | 0.46 | 0.65 | 0.40 | 1.60* |
| 84 | 1.00 | 1.21 | 0.67 | 0.76 | 0.64 | 1.01* | 0.70 |
| 85 | 0.38 | 0.41 | 0.31 | 0.24 | 0.19 | 0.29 | 0.29 |
| 86 | 0.60 | 0.50 | 0.41 | 0.25 | 0.34 | 0.35 | 0.56 |
| 87 | 0.60 | 0.61 | 0.53 | 0.33 | 0.45 | 0.36 | 0.96 |
| 88 | 0.66 | 0.50 | 0.35 | 0.24 | 0.27 | 0.25 | 0.32 |
| 89 | 0.74 | 0.40 | 0.40 | 0.26 | 0.37 | 0.29 | 0.61 |
| 90 | 0.39 | 0.38 | 0.31 | 0.24 | 0.22 | 0.27 | 0.36 |
| 91 | 1.28 | 1.29 | 0.75 | 0.53 | 0.73 | 0.66 | 1.36* |
| 92 | 1.01 | 0.53 | 0.38 | 0.41 | 0.70 | 0.57 | 1.78* |
| 93 | 0.55 | 0.50 | 0.37 | 0.40 | 0.52 | 0.52 | 0.78 |
| 94 | 0.49 | 0.44 | 0.38 | 0.24 | 0.40 | 0.24 | 0.60 |
| 95 | 0.63 | 0.59 | 0.67 | 0.35 | 0.34 | 0.37 | 0.39 |
| Average | 0.65 | 0.63 | 0.43 | 0.36 | 0.53 | 0.46 | 0.80 |

Table 5 shows the corresponding figures for the samples taken from people carrying out various different roles working in abattoirs. Responses marked * correspond to values above the average for the WHO TB-negative set. No values above the average for the TB-positive set were seen.

Table 5: Responses of serum samples from abattoir workers. Columns 2-8 represent the responses in the assay with antigens 1-7. Column 9 is the total of these values. Values marked * are above the average for the WHO-negatives for a particular antigen.

TABLE 5

Responses of serum samples from abattoir workers. Columns 2-8 represent the responses in the assay with antigens 1-7. Column 9 is the total of these values. Values marked * are above the average for the WHO-negatives for a particular antigen.

|  | Antigens | | | | | | | |
|---|---|---|---|---|---|---|---|---|
|  | 1 | 2 | 3 | 4 | 5 | 6 | 7 | Total |
| WHO + average | 2.97 | 2.58 | 2.53 | 2.19 | 2.83 | 2.45 | 3.11 | 18.67 |
| WHO − average | 1.39 | 1.36 | 0.99 | 0.96 | 0.99 | 0.96 | 1.00 | 7.65 |
| 96 | 0.59 | 0.47 | 0.35 | 0.25 | 0.59 | 0.37 | 0.36 | 2.97 |
| 97 | 1.26 | 0.71 | 0.74 | 0.45 | 1.36* | 0.60 | 0.99 | 6.10 |
| 98 | 0.73 | 1.36* | 0.60 | 0.67 | 0.65 | 1.20* | 0.37 | 5.58 |
| 99 | 0.36 | 0.35 | 0.27 | 0.16 | 0.47 | 0.29 | 0.25 | 2.15 |
| 100 | 0.43 | 0.42 | 0.30 | 0.17 | 0.39 | 0.25 | 0.29 | 2.24 |
| 101 | 1.65* | 1.06 | 1.07* | 0.64 | 1.79* | 1.15* | 1.12* | 8.47 |
| 102 | 0.44 | 0.44 | 0.42 | 0.21 | 0.41 | 0.31 | 0.28 | 2.50 |
| 103 | 0.49 | 0.39 | 0.35 | 0.14 | 0.54 | 0.27 | 0.51 | 2.69 |
| 104 | 0.36 | 0.31 | 0.29 | 0.13 | 0.36 | 0.26 | 0.24 | 1.94 |
| 105 | 0.32 | 0.49 | 0.29 | 0.25 | 0.37 | 0.50 | 0.22 | 2.45 |

TABLE 5-continued

Responses of serum samples from abattoir workers. Columns 2-8 represent the
responses in the assay with antigens 1-7. Column 9 is the total of these values. Values marked *
are above the average for the WHO-negatives for a particular antigen.

|  | Antigens | | | | | | | |
|---|---|---|---|---|---|---|---|---|
|  | 1 | 2 | 3 | 4 | 5 | 6 | 7 | Total |
| 106 | 0.47 | 0.45 | 0.39 | 0.20 | 0.53 | 0.39 | 0.33 | 2.76 |
| 107 | 0.33 | 0.28 | 0.24 | 0.16 | 0.43 | 0.30 | 0.28 | 2.03 |
| 108 | 0.66 | 0.39 | 0.26 | 0.16 | 0.43 | 0.30 | 0.46 | 2.66 |
| 109 | 0.69 | 0.51 | 0.23 | 0.20 | 0.40 | 0.30 | 0.47 | 2.80 |
| 110 | 0.97 | 1.75* | 0.50 | 0.88 | 0.62 | 1.49* | 0.63 | 6.84 |
| 111 | 0.93 | 0.70 | 0.26 | 0.33 | 0.57 | 0.64 | 0.70 | 4.13 |
| 112 | 0.55 | 0.51 | 0.23 | 0.28 | 0.37 | 0.35 | 0.42 | 2.71 |
| 113 | 0.52 | 0.36 | 0.22 | 0.22 | 0.32 | 0.22 | 0.43 | 2.29 |
| 114 | 0.70 | 0.39 | 0.22 | 0.27 | 0.33 | 0.28 | 0.40 | 2.60 |
| 115 | 1.33 | 1.29 | 0.56 | 0.42 | 1.24* | 0.74 | 1.18* | 6.76 |
| 116 | 0.41 | 0.96 | 0.11 | 0.40 | 0.19 | 0.57 | 0.25 | 2.90 |
| 117 | 0.56 | 0.37 | 0.20 | 0.17 | 0.33 | 0.23 | 0.43 | 2.29 |
| 118 | 0.60 | 0.40 | 0.25 | 0.23 | 0.32 | 0.26 | 0.45 | 2.50 |
| 119 | 0.57 | 0.64 | 0.46 | 0.23 | 0.66 | 0.41 | 0.55 | 3.51 |
| 120 | 0.36 | 0.32 | 0.20 | 0.20 | 0.32 | 0.26 | 0.44 | 2.10 |
| 121 | 1.09 | 0.93 | 0.33 | 0.29 | 0.61 | 0.61 | 1.00* | 4.85 |
| 122 | 0.53 | 0.48 | 0.20 | 0.19 | 0.36 | 0.33 | 0.43 | 2.50 |
| 123 | 0.36 | 0.50 | 0.17 | 0.31 | 0.24 | 0.39 | 0.31 | 2.28 |
| 124 | 0.31 | 1.37* | 0.22 | 0.82 | 0.41 | 1.53* | 0.47 | 5.13 |
| 125 | 0.45 | 0.42 | 0.19 | 0.23 | 0.29 | 0.26 | 0.37 | 2.21 |
| 126 | 0.96 | 1.63* | 0.46 | 0.78 | 1.03* | 0.97 | 1.31* | 7.15 |
| 127 | 0.46 | 0.29 | 0.15 | 0.17 | 0.22 | 0.18 | 0.28 | 1.74 |
| 128 | 0.68 | 0.51 | 0.29 | 0.32 | 0.48 | 0.36 | 0.60 | 3.24 |
| 129 | 0.85 | 0.82 | 0.48 | 0.35 | 0.80 | 0.57 | 0.76 | 4.63 |
| 130 | 0.59 | 0.51 | 0.54 | 0.27 | 0.55 | 0.48 | 0.38 | 3.33 |
| Average | 0.64 | 0.65 | 0.34 | 0.32 | 0.54 | 0.50 | 0.51 | 3.52 |

In this case only one of the samples gave total responses exceeding the values of the WHO-negative samples.

In contrast, the data for the farmer's samples (Table 6) show 10 out of 44 samples with total values above the WHO-negative total, a large number of individual values above the corresponding values for the WHO samples. Moreover, the highest ranked sample in this case gave a total value higher than the average of the TB+ samples from the WHO. A significant number of individual responses were also above the WHO+ average for a particular antigen.

Table 6: Responses from people identified as farmers. Columns as in Table 2. Columns 2-8 represent the responses in the assay with antigens 1-7. Column 9 is the total of these values. Values marked * are above the average for the WHO-negatives for a particular antigen.

TABLE 6

Responses from people identified as farmers. Columns as in Table 2. Columns 2-8
represent the responses in the assay with antigens 1-7. Column 9 is the total of these values.
Values marked * are above the average for the WHO-negatives for a particular antigen.

|  | Antigens | | | | | | | |
|---|---|---|---|---|---|---|---|---|
|  | 1 | 2 | 3 | 4 | 5 | 6 | 7 | Total |
| WHO + average | 2.97 | 2.58 | 2.53 | 2.19 | 2.83 | 2.45 | 3.11 | 18.67 |
| WHO − average | 1.39 | 1.36 | 0.99 | 0.96 | 0.99 | 0.96 | 1.00 | 7.65 |
| 1 | 2.93* | 3.16* | 2.33* | 2.76* | 3.07* | 2.95* | 3.18* | 20.37 |
| 2 | 3.64* | 1.67* | 1.34* | 1.31* | 2.91* | 2.12* | 3.81* | 16.79 |
| 3 | 2.62* | 2.07* | 2.78* | 1.01* | 2.46* | 0.94 | 3.13* | 15.01 |
| 4 | 2.08* | 1.49* | 0.92* | 1.35* | 2.23* | 1.32* | 3.05* | 12.44 |
| 5 | 2.45* | 1.65* | 1.71* | 1.17* | 0.98 | 1.36* | 2.97* | 12.30 |
| 6 | 1.59* | 3.10* | 0.60 | 2.36* | 0.74 | 2.88* | 0.90 | 12.18 |
| 7 | 2.53* | 1.14 | 2.46* | 0.99* | 1.44* | 0.97 | 2.03* | 11.55 |
| 8 | 1.92* | 1.27 | 1.45* | 0.68 | 1.88* | 1.33* | 1.33* | 9.86 |
| 9 | 2.10* | 1.14 | 1.32* | 0.65 | 1.18* | 1.02 | 2.10* | 9.51 |
| 10 | 1.80* | 1.07 | 0.20 | 1.13* | 0.76 | 0.95 | 1.89* | 7.80 |
| 11 | 1.44* | 0.91 | 0.69 | 0.65 | 1.13* | 0.86 | 1.74* | 7.42 |
| 12 | 1.32 | 0.91 | 0.62 | 0.46 | 0.70 | 0.79 | 1.44* | 6.23 |
| 13 | 1.13 | 0.83 | 0.64 | 0.46 | 0.79 | 0.45 | 1.37* | 5.68 |
| 14 | 0.74 | 0.94 | 0.25 | 0.93* | 0.63 | 1.15* | 0.78 | 5.42 |
| 15 | 1.02 | 0.88 | 0.56 | 0.46 | 0.68 | 0.61 | 1.18* | 5.38 |
| 16 | 1.21 | 0.50 | 0.65 | 0.35 | 0.78 | 0.41 | 1.34* | 5.23 |
| 17 | 1.08 | 0.74 | 0.62 | 0.56 | 0.68 | 0.61 | 0.93 | 5.21 |
| 18 | 0.70 | 0.62 | 0.44 | 0.42 | 0.55 | 0.49 | 1.37* | 4.60 |

TABLE 6-continued

Responses from people identified as farmers. Columns as in Table 2. Columns 2-8 represent the responses in the assay with antigens 1-7. Column 9 is the total of these values. Values marked * are above the average for the WHO-negatives for a particular antigen.

| | Antigens | | | | | | | |
|---|---|---|---|---|---|---|---|---|
| | 1 | 2 | 3 | 4 | 5 | 6 | 7 | Total |
| 19 | 0.71 | 0.63 | 0.53 | 0.52 | 0.43 | 0.71 | 1.07* | 4.59 |
| 20 | 0.64 | 0.47 | 0.47 | 0.46 | 0.68 | 0.61 | 1.07* | 4.40 |
| 21 | 0.51 | 0.85 | 0.36 | 0.48 | 0.46 | 0.84 | 0.81 | 4.31 |
| 22 | 0.87 | 0.46 | 0.57 | 0.38 | 0.71 | 0.43 | 0.61 | 4.02 |
| 23 | 0.64 | 0.88 | 0.45 | 0.48 | 0.43 | 0.49 | 0.59 | 3.97 |
| 24 | 0.64 | 0.56 | 0.43 | 0.29 | 0.64 | 0.54 | 0.87 | 3.97 |
| 25 | 0.85 | 0.41 | 0.27 | 0.37 | 0.52 | 0.47 | 0.91 | 3.79 |
| 26 | 0.46 | 0.33 | 0.43 | 0.22 | 0.69 | 0.34 | 0.69 | 3.16 |
| 27 | 0.62 | 0.51 | 0.39 | 0.30 | 0.41 | 0.27 | 0.65 | 3.14 |
| 28 | 0.40 | 0.71 | 0.18 | 0.74 | 0.27 | 0.47 | 0.27 | 3.05 |
| 29 | 0.49 | 0.34 | 0.46 | 0.24 | 0.31 | 0.33 | 0.79 | 2.96 |
| 30 | 0.53 | 0.29 | 0.40 | 0.39 | 0.41 | 0.29 | 0.59 | 2.89 |
| 31 | 0.65 | 0.39 | 0.38 | 0.34 | 0.42 | 0.35 | 0.36 | 2.89 |
| 32 | 0.48 | 0.30 | 0.39 | 0.30 | 0.38 | 0.36 | 0.64 | 2.85 |
| 33 | 0.30 | 0.28 | 0.35 | 0.27 | 0.60 | 0.35 | 0.65 | 2.81 |
| 34 | 0.58 | 0.58 | 0.45 | 0.21 | 0.31 | 0.29 | 0.29 | 2.72 |
| 35 | 1.06 | 0.41 | 0.30 | 0.20 | 0.23 | 0.23 | 0.24 | 2.69 |
| 36 | 0.39 | 0.37 | 0.32 | 0.43 | 0.42 | 0.34 | 0.34 | 2.61 |
| 37 | 0.39 | 0.29 | 0.09 | 0.23 | 0.51 | 0.33 | 0.75 | 2.59 |
| 38 | 0.34 | 0.34 | 0.22 | 0.24 | 0.33 | 0.28 | 0.41 | 2.15 |
| 39 | 0.22 | 0.26 | 0.21 | 0.23 | 0.39 | 0.35 | 0.46 | 2.13 |
| 40 | 0.32 | 0.27 | 0.30 | 0.24 | 0.40 | 0.26 | 0.28 | 2.07 |
| 41 | 0.28 | 0.21 | 0.30 | 0.20 | 0.35 | 0.24 | 0.44 | 2.03 |
| 42 | 0.21 | 0.28 | 0.17 | 0.23 | 0.26 | 0.29 | 0.41 | 1.85 |
| 43 | 0.43 | 0.35 | 0.21 | 0.19 | 0.16 | 0.19 | 0.22 | 1.74 |
| 44 | 0.22 | 0.20 | 0.14 | 0.17 | 0.26 | 0.23 | 0.34 | 1.56 |
| Average | 1.03 | 0.80 | 0.64 | 0.59 | 0.79 | 0.71 | 1.12 | 5.68 |

These results clearly show differences in the responses for farmers from the other sub-sets. This may indicate a high antibody burden and a possible link to existing or developing infection. Moreover, the results suggest there is a very significant potential that routine measurement of responses of antibodies in serum to lipid antigens can provide a rapid means for guiding public health practices, identifying the early stages of infection and allowing early treatment and controlling exposure or disease in at risk population groups.

The invention claimed is:

1. A method of determining whether an individual is infected with mycobacteria, the method comprising:
 (a) providing a system comprising a substrate which comprises at least two different antigens at different positions on the substrate,
  each of the two or more antigens being selected from a group consisting of the following classes of compounds:
  (i) mycolic acids obtained from natural sources;
  (ii) synthetically prepared mycolic acids;
  (iii) salts of mycolic acids;
  (iv) esters of mycolic acids (i) and/or (ii);
  (v) sulfur-containing mycolic acid compounds and/or salts or esters thereof;
  (vi) simple structural analogues of mycolic acids and/or salts or esters thereof; and
  (vii) mycolic acid wax esters and/or salts or esters thereof;
 (b) introducing a sample obtained from the individual into the system and into contact with each of the at least two different antigens; and
 (c) adding a reagent comprising either:
  (i) colloidal gold particles carrying a secondary antibody which forms a chemical interaction with the biomarker; or
  (ii) a colorimetric substrate and the colour change is detected using an enzyme-linked secondary antibody in combination with the colorimetric substrate, wherein the secondary antibody forms a chemical interaction with the biomarker;
 (d) washing off any nonbound excess reagent; and
 (e) detecting the presence or absence of the binding of a biomarker in the sample with each antigen at each position on the substrate,
 wherein step (e) involves qualitatively observing or quantitatively measuring a colour change on the substrate; and wherein the presence or absence of a colour change at two or more different positions on the substrate in combination leads to the determination of whether or not an individual is infected with a mycobacterial disease,
 wherein a colour change is observed on the substrate when the biomarker is present in the sample and binds with an antigen and is therefore present on the substrate, and is not observed when the biomarker is absent from the sample, does not bind with an antigen, and therefore is not present on the substrate;
 and the biomarker is an antibody indicative of infection with a mycobacterial disease.

2. The method according to claim 1 wherein each antigen is at least 90% pure.

3. The method according to claim 1 wherein the system comprises from 6 to 12 different antigens.

4. The method according to claim 1 wherein the system comprises:
 (a) a trehalose monomycolate antigen; and/or
 (b) a trehalose dimycolate antigen; and/or
 (c) a mycolic acid wax ester antigen; and/or
 (d) a glucose monomycolate antigen.

5. The method according to claim 2, wherein the system comprises (i) an arabinose mycolate antigen.

6. The method according to claim 1 which determines the likelihood that an individual is infected with one or more species of mycobacteria.

7. The method according to claim 1 which is a method of determining whether an individual is infected with *Mycobacterium avium paratuberculosis*; and wherein at least one of the antigens is a wax ester or a derivative thereof.

8. A kit for determining the presence or absence of a biomarker in a sample, the kit comprising:
   (x) a substrate which comprises two or more different antigens at different positions, the two or more different antigens each being selected from the group consisting of the following classes of compounds:
      (i) mycolic acids obtained from natural sources;
      (ii) synthetically prepared mycolic acids;
      (iii) salts of mycolic acids;
      (iv) esters of mycolic acids (i) and/or (ii);
      (v) sulfur-containing mycolic acid compounds and/or salts or esters thereof;
      (vi) simple structural analogues of mycolic acids and/or salts or esters thereof; and
      (vii) mycolic acid wax esters and/or salts or esters thereof; and
   (y) a composition comprising a secondary antibody which forms a chemical interaction with the biomarker,
   wherein the secondary antibody comprises an enzyme linked secondary antibody and the kit further comprises a composition comprising a colorimetric substrate for the enzyme; or
   wherein the composition comprising a secondary antibody is a composition comprising particles of colloidal gold wherein the colloidal gold particles carry a secondary antibody on their surface.

9. The kit of claim 8, wherein the chemical interaction is a polar interaction or a non-polar interaction.

10. The kit of claim 8, wherein the chemical interaction is a dipole-dipole interaction, a hydrogen bond, or a Van der Waals force.

11. The kit of claim 8, wherein the chemical interaction is a hydrogen bond.

* * * * *